(12) United States Patent
Ramael

(10) Patent No.: US 8,227,380 B2
(45) Date of Patent: *Jul. 24, 2012

(54) METHOD AND KIT FOR DETECTING COMPONENTS IN A SAMPLE

(76) Inventor: Marc Ramael, Haasdonk (BE)

( * ) Notice: Subject to any disclaimer, the term of this patent is extended or adjusted under 35 U.S.C. 154(b) by 1181 days.

This patent is subject to a terminal disclaimer.

(21) Appl. No.: 11/587,710

(22) PCT Filed: Apr. 29, 2004

(86) PCT No.: PCT/EP2004/004547
§ 371 (c)(1),
(2), (4) Date: Oct. 26, 2006

(87) PCT Pub. No.: WO2005/111619
PCT Pub. Date: Nov. 24, 2005

(65) Prior Publication Data
US 2008/0269064 A1  Oct. 30, 2008

(51) Int. Cl.
*C40B 20/04* (2006.01)
*C40B 30/04* (2006.01)
*G01N 33/53* (2006.01)

(52) U.S. Cl. .............. 506/4; 506/9; 435/7.5
(58) Field of Classification Search ............ 506/4, 9; 435/7.5
See application file for complete search history.

(56) References Cited

U.S. PATENT DOCUMENTS

| | | | |
|---|---|---|---|
| 5,691,207 A | 11/1997 | Holtlund et al. | |
| 6,905,816 B2 * | 6/2005 | Jacobs et al. | 435/5 |
| 6,924,094 B1 * | 8/2005 | Gingeras et al. | 435/5 |
| 7,176,036 B2 * | 2/2007 | Wang et al. | 436/524 |
| 7,442,339 B2 * | 10/2008 | Sundararajan et al. | 422/82.05 |
| 7,531,305 B2 * | 5/2009 | Thunnissen et al. | 435/6 |
| 2002/0000398 A1 | 1/2002 | Skold | |
| 2003/0186274 A1 | 10/2003 | Limoges et al. | |
| 2003/0203394 A1 * | 10/2003 | Eichen et al. | 435/6 |

OTHER PUBLICATIONS

Bronckers et al., 1987, Immunolocalization of Gla proteins (Osteocalcin) in Rat tooth germs: Comparision between indirect immunofluorescence, peroxidase-antiperoxidase, avidin-biotin-peroxidase complex, and avidin-biotin-gold complex with silver enhancement, J Histochemistry and Cytochemistry, 35(8): 825-830.*

Bronckers, et al. "Immunolocalization of Gla Proteins (Osteocalcin) in Rat Tooth Germs: Comparison Between Indirect Immunofluorescence, Peroxidase-Antiperoxidase, Avidin-Biotin-Peroxidase Complex, and Avidin-Biotin-Gold Complex with Silver Enhancement," *The Journal of Histochemistry and Cytochemistry*, vol. 35, No. 8, pp. 825-830, 1987.

Dankner, et al. "Detection of Human Cytomegalovirus by Immunogold and Silver Enhancement," *The Journal of Hisotechnology*, vol. 12, No. 1, pp. 9-13, Mar. 1989.

Skutelsky, et al. "The Use of Avidin-Gold Complex for Light Microscopic Localization of Lectin Receptors," *Histochemistry*, vol. 86, pp. 291-295, 1987.

* cited by examiner

*Primary Examiner* — Amber D Steele
(74) *Attorney, Agent, or Firm* — Knobbe, Martens, Olson & Bear, LLP

(57) ABSTRACT

Methods and a kit for use in the detection of a component in a sample on a solid support are disclosed which use a conjugate and polymer having metal particles of diameter in the nanometer range (that is between 0.1 and 500 nm). Methods and a kit for detection of a component in a sample on a solid support which have a conjugate and optionally a polymer bound to one or more supermagnetic particles are also disclosed. The methods and kits may be used for enhancing in vivo imaging and microscopy.

15 Claims, 2 Drawing Sheets

A Step a): Applying one or more samples onto a solid support:
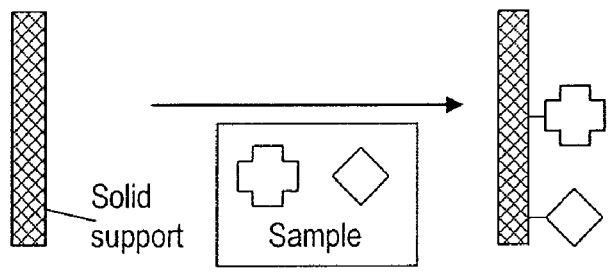
B Step b): Contacting the solid support with one or more biotin-labeled probes:
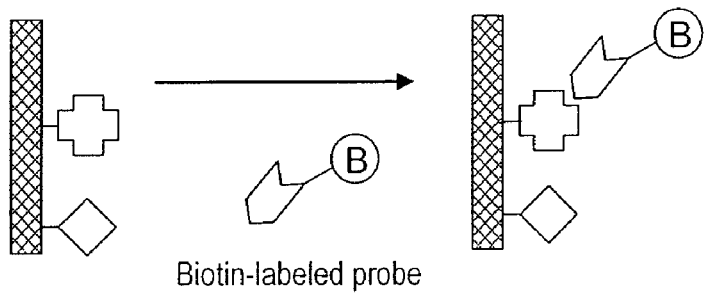
Biotin-labeled probe
C Step c): Contacting the solid support with a streptavidin-metal particle complex:
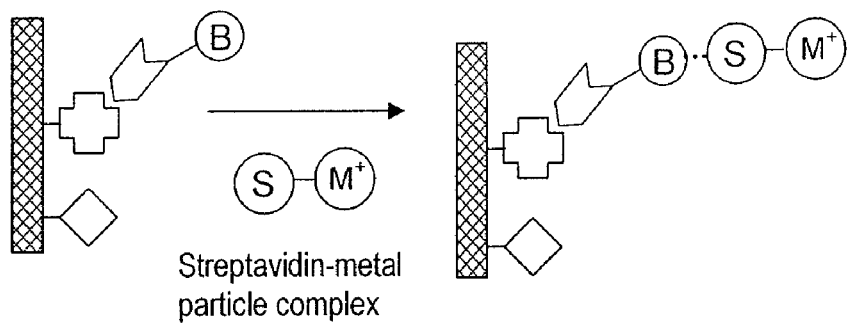
Streptavidin-metal particle complex

D Step d): Contacting the solid support with a conjugate comprising one or more biotins, one or more polymers, and metal particles bound to said polymer:
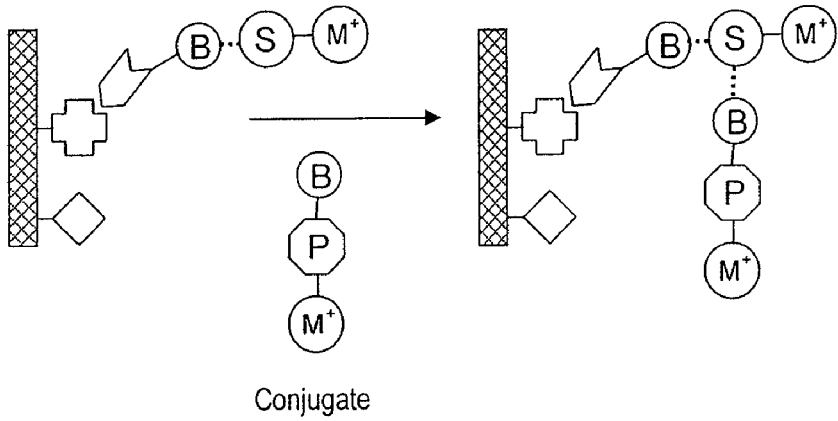
Conjugate
E Step f): Reading the solid support to quantitatively and/or qualitatively detect said component and variations thereof:
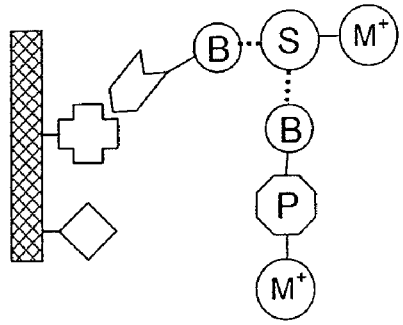

SEQUENCE LISTING

<160> NUMBER OF SEQ ID NOS: 3

<210> SEQ ID NO 1
<211> LENGTH: 27
<212> TYPE: DNA
<213> ORGANISM: Artificial Sequence
<220> FEATURE:
<223> OTHER INFORMATION: Target

<400> SEQUENCE: 1
ggattattgt taaatattga taaggat                                        27

<210> SEQ ID NO 2
<211> LENGTH: 15
<212> TYPE: DNA
<213> ORGANISM: Artificial Sequence
<220> FEATURE:
<223> OTHER INFORMATION: Visualisation oligo

<400> SEQUENCE: 2
atccttatca atatt                                                    15

<210> SEQ ID NO 3
<211> LENGTH: 12
<212> TYPE: DNA
<213> ORGANISM: Artificial Sequence
<220> FEATURE:
<223> OTHER INFORMATION: Oligo op drager

<400> SEQUENCE: 3
taacaataat cc                                                       12

METHOD AND KIT FOR DETECTING COMPONENTS IN A SAMPLE

RELATED APPLICATIONS

This application is the U.S. National Phase under 35 U.S.C. §371 of International Application PCT/EP2004/004547, filed Apr. 29, 2004.

JOINT RESEARCH AGREEMENT DISQUALIFICATION

The claimed invention was made by or on behalf of Marc Ramael and Jean-Paul Sanders, who were parties to a joint research agreement that was in effect on or before the date the claimed invention was made. The claimed invention was made as a result of activities undertaken within the scope of the joint research agreement.

BACKGROUND TO THE INVENTION

Micro-arrays are tools for protein, DNA and RNA molecular diagnostics, often used for the detection of nucleic acids and proteins. Such parallellisation techniques, enable the investigation of several thousands of sequences in one reaction or experiment. Most applications are focused on expression profiling for measuring adequately the expression of several thousands genes of interest. Presently, detection of molecular binding on micro-arrays is effected by use of special fluorescent dyes such as Cy3 and Cy5. However, the accuracy and reproducibility of such techniques is limited by the stability of the fluorescent marker.

Sequence-selective DNA detection has become increasingly important as scientists unravel the genetic basis of disease and use this new information to improve medical diagnosis and treatment. DNA hybridization tests on oligonucleotide-modified substrates are commonly used to detect the presence of specific DNA sequences in solution. The developing promise of combinatorial DNA arrays for probing genetic information illustrates the importance of these heterogeneous sequence assays to future science. In most assays, the hybridization of fluorophore-labeled targets to surface bound probes is monitored by fluoresecence microscopy or densitometry. Although fluorescence detection is very sensitive, its use is limited by the expense of the experimental equipment and by background emissions from most common substrates. In addition, the selectivity of labeled oligonucleotide targets for perfectly complementary probes over those with single base mismatches is poor, preventing the use of surface hybridization tests for detection of single nucleotide polymorphisms.

Another disadvantage is that the evaluation of processed fluorescence based micro-arrays needs highly expensive laser scanning devices, as well as highly sophisticated software for analysing the data generated by the laser scanning devices. Such equipment is not available to all laboratories, and certainly not to laboratories with limited resources. Thus a major drawback of this technology the capital expense, and its use restricted to well resourced laboratories.

A limited number of prior art documents describe detection methods and/or reagents for use in solid-phase assays, but each is associated with numerous disadvantages. Enzymatic methods or gold-based detection method on micro-arrays are described in WO 00/72018, EP 1164201, EP 1096024, WO 01/77372A2, US 2001/0010906A1. The patent application number WO 00/72018 describes the use of biotinylated DNA on micro-array using streptavidin labelled gold. Other patent documents such as EP 1164201, EP 1096024 and WO 01/77372A2 describe methods and kits for detection and quantification of homologue nucleotides, method and kit for diagnosis and quantification using sandwich hybridisation on solid carrier (US 2001/0010906A1). Patent document EP 1164201 describes the use of inverted detection for identifying and/or quantifying nucleotide target sequences on biochips using micro-fluidity techniques. Patent document EP 10960245 describes a method for detection of homologue sequences after multiplex PCR for detecting *Staphylococcus* microorganisms. Patent documents AU8366001, AU7547501, CA2397280, WO 01/96604 and WO 99/20789 describe a detection technique using streptavidin labelled gold particles of at least 80 nm for visualisation of bound nucleic acids on micro-array. Patent document U.S. Pat. No. 6,451,980 describes a technique for signal enhancement using a bi-specific antibody-polymer probe, wherein one part of said probe recognises the antigen and the other part is directed against DTPA (diethylenepentaacteic acid). Patent document WO 02/06511 (Genisphere) describes an amplification technique applicable to micro-arrays using a DNA dendrimer-based approach. Patent document WO 01/36681 (Digene) discloses a technology for detecting DNA/RNA hybrids on micro-arrays using a monoclonal antibody directed specifically to RNA/DNA hybrids with visualisation using fluorescent dyes. Patent document WO 96/14314 (DAKO) describes the use of a specific monoclonal antibody for detecting DNA/PNA nucleic acid hybrids. The use of lectins or dextran coated with biotin molecules for use specially in in situ hybridization is disclosed in patent document EP0151492 (ENZO).

A detection scheme which improves upon the simplicity, sensitivity and selectivity of methods in the art could allow the full potential of combinatorial sequence analysis to be realized. Therefore, for reading and analysing arrays at a low cost, with high sensitivity and reproducibility, there is a need for a technique which overcomes the problems of the art.

For generalizing the use of this technology, it would be advantageous to have a visualization technique that enables the investigator to evaluate the hybridization results with the naked eye without use of laser scanning devices or other kind of expensive visualization equipment. Alternatively, a system which enables the use of low cost readers e.g. those which detect electrical conductance and/or changes in magnetic flux would help sensitive array-type assaying become more cost effective as a research and diagnostic tool.

SUMMARY OF THE INVENTION

One embodiment of the present invention is a method for quantitatively and/or qualitatively detecting one or more components in a sample, each component capable of binding to a probe, comprising steps in the following order:
(a) applying one or more samples onto a solid support,
(b) contacting solid support with one or more biotin-labeled probes,
(c) contacting solid support with streptavidin-metal particle complex,
(d) contacting solid support with conjugate comprising:
  one or more biotins,
  one of more polymers, and
  metal particles bound to said polymer,
(e) optionally contacting the solid support with metal enhancement reagent, and
(f) reading the solid support to quantitatively and/or qualitatively detect said component.

Another embodiment of the present invention is a method as described above wherein step
(a) is replaced by:
(a) applying one or more probes onto solid support, and step (b) is replaced by:
(b) contacting solid support with biotin-labelled sample.

Another embodiment of the present invention is a method as described above wherein step (a) is preceded by:
(a0) applying one or more probes onto solid support.

Another embodiment of the present invention is a method as described above wherein the solid support is supplied with probe pre-applied, and step (a) of the second embodiment above or step (a0) of the third embodiment above is not performed by the user.

Another embodiment of the present invention is a method as described above wherein the reading of step (f) comprises the use of a colour chart.

Another embodiment of the present invention is a method as described above wherein the reading of step (f) comprises a use of a device suitable for detecting changes in conductance and/or current across the solid support.

Another embodiment of the present invention is a method as described above wherein the reading of step (f) comprises a use of a device suitable for detecting changes in magnetic field on the solid support.

Another embodiment of the present invention is a method as described above wherein the reading of step (f) comprises a use of a device suitable for detecting changes in surface plasmon resonance on the solid support.

Another embodiment of the present invention is a method as described above wherein the metal enhancement reagent of step (e) is a silver enhancement reagent Another embodiment of the present invention is a kit for quantitatively and/or qualitatively detecting one or more components in a sample, each component capable of binding to a probe, comprising:
  streptavidin-metal particle complex, and
  solid support, Another embodiment of the present invention is a kit as described above further comprising:
  conjugate comprising:
    biotin,
    polymer, and
    metal particles bound to said polymer, Another embodiment of the present invention is a kit as described above further comprising one or more probes.

Another embodiment of the present invention is a kit as described above wherein said probes are biotinylated.

Another embodiment of the present invention is a kit as described above wherein said solid support preloaded with one or more probes.

Another embodiment of the present invention is a method or a kit as described above wherein the polymer of a conjugate is a biologically inert polymer, capable of binding to one or more metal particles.

Another embodiment of the present invention is a method or a kit as described above wherein a polymer is any of albumin or dextran.

Another embodiment of the present invention is a method or a kit as described above wherein conjugate comprises are one or more particles of gold, silver, iron, nickel, gadolinium, lead, uranium, caesium, platinum, rhodium, technetium, tellurium, selenium, silicon, silicium, cupper, tin, rhenium, europium, aluminium, germanium, chromium, cadmium, niobium, titanium, magnesium, manganese, molybdenum, antimony, americium, lithium, and/or wolfram.

Another embodiment of the present invention is a method or a kit as described above wherein conjugate comprises one or more gold particles.

Another embodiment of the present invention is a method or a kit as described above wherein a conjugate comprises one or more silver particles.

Another embodiment of the present invention is a method or a kit as described above wherein the metal particles of conjugate have a diameter between 0.6 to 40 nm.

Another embodiment of the present invention is a kit as described above for use in a method as described above.

One embodiment of the present invention is a method for enhancing the imaging of one or more components in a system by magnetic resonance imaging, each component capable of binding to a probe, comprising the steps of:
(i) adding one or more biotin-labelled probes to a system,
(ii) adding streptavidin-metal particle complex to said system, and
(iii) obtaining an image using magnetic resonance imaging.

Another embodiment of the present invention is a kit for enhancing the imaging of one or more components in a system by magnetic resonance imaging, each component being capable of binding to a probe, comprising streptavidin-metal particle complex.

Another embodiment of the present invention is a kit as described above further comprising one or more biotin-labelled probes.

Another embodiment of the present invention is a kit as described above for use in a method of enhancing the imaging of one or more components in a system as described above.

Another embodiment of the present invention is a method or a kit as described above wherein said probe is an antibody, nucleic acid, peptide nucleic acid, polypeptide or peptide ligand.

Another embodiment of the present invention is a method or a kit as described above wherein steptavidin-metal particle complex comprises one or more particles of gold, silver, iron, nickel, gadolinium, lead, uranium, caesium, platinum, palladium, rhodium, technetium, tellurium, selenium, silicon (silicium), cupper, tin, rhenium, europium, aluminium, germanium, chromium, cadmium, niobium, titanium, magnesium, manganese, molybdenum, antimony, americium, lithium, and/or wolfram.

Another embodiment of the present invention is a method or a kit as described above wherein steptavidin-metal particle complex comprises one or more gold particles.

Another embodiment of the present invention is a method or a kit as described above wherein steptavidin-metal particle complex comprises one or more silver particles.

Another embodiment of the present invention is a method or a kit as described above wherein the metal particles of steptavidin-metal particle complex have a diameter between 0.6 to 40 nm.

Another embodiment of the present invention is a method or a kit as described above wherein said streptavidin-metal particle complex comprises streptavidin and/or avidin.

Another embodiment of the present invention is a method or a kit as described above wherein the streptavidin-metal particle complex and/or conjugate comprise one or more superparamagnetic particles.

Another embodiment of the present invention is a method or a kit as described above wherein the streptavidin-metal particle complex comprises one or more superparamagnetic particles, and wherein steps (d) and (e) are not performed.

Another embodiment of the present invention is a method or a kit as described above wherein said superparamagnetic particles comprise iron oxide.

Another embodiment of the present invention is a method or a kit as described above wherein the iron oxide content of a superparamagnetic particle is between 30 and 80%.

Another embodiment of the present invention is a method or a kit as described above wherein said superparamagnetic particles have a diameter between 50 and 400 nm.

Another embodiment of the present invention is a method or a kit as described above wherein at least one probe is capable of binding to Human Papillomavirus.

Another embodiment of the present invention is a method or a kit as described above wherein said probe is capable of binding to Human Papillomavirus coat polypeptide.

Another embodiment of the present invention is a method or a kit as described above for detecting, diagnosing and/or monitoring the progress of a Human Papillomavirus (HPV) infection.

Another embodiment of the present invention is a method or a kit as described above wherein at least one probe is capable of binding to a gene selected from the group consisting of HPV 16, HPV18, HPV 31, HPV 33, HPV 35, HPV 52 and HPV 58.

Another embodiment of the present invention is a method or a kit as described above wherein said probe is capable of binding to a component listed in Table 1.

Another embodiment of the present invention is a method or a kit as described above for detecting, diagnosing and/or monitoring the progress of or susceptibility to one or more of the disease states in humans as listed in Table 1, by detecting a polypeptide and/or nucleic acid corresponding to a component therein.

Another embodiment of the present invention is a method or a kit as described above wherein at least one probe is capable of binding to any of HCV, HIV, HBV, HTLV, mycobacteria, or *Staphylococcus aureus*.

Another embodiment of the present invention is a method or a kit as described above for detecting, diagnosing and/or monitoring the progress infections caused by one or more of one or more of HCV, HIV, HBV, HTLV, mycobacteria, or *Staphylococcus aureus*.

Another embodiment of the present invention is a method or a kit as described above wherein at least one probe is capable of binding to one or more of beta-amyloids, hTAU, phosphoTAU and APOE Another embodiment of the present invention is a method or a kit as described above for use in detecting, diagnosing and/or monitoring the progress neurodegenerative diseases.

Another embodiment of the present invention is a method or a kit as described above wherein at least one probe is capable of binding to one or more of ANA, Jo-1, Myeloperoxidase, RNP, Scl-70, Sm, SS-A, IgE, IgG-subclasses and circulating antibodies.

Another embodiment of the present invention is a method or a kit as described above for use in detecting, diagnosing and/or monitoring the progress of malignant diseases, autoimmunity or allergy related diseases.

Another embodiment of the present invention is a method or a kit as described above wherein at least one probe is capable of binding to microorganism contaminants of drinking water.

Another embodiment of the present invention is a method or a kit as described above for environmental testing of water for bacteria.

Another embodiment of the present invention is a method or a kit as described above for use in environmental testing of food components for genetically modified components, *listeria* and *salmonella*.

Another embodiment of the present invention is a method for staining components in cell and/or tissue sections, said staining suitable for visualisation using microscopy comprises the following steps:
A) incubating section with one or more biotinylated probes directed against said components,
B) incubating section with streptavidin-metal particle complex,
C) incubating section with conjugate comprising:
  one or more biotins,
  one or more polymers, and
  metal particles bound to said polymer, and
D) optionally incubating the section with metal enhancement reagent.

BRIEF DESCRIPTION OF THE DRAWING

These and other feature of this invention will now be described with reference to the drawings of preferred embodiments which are intended to illustrate and not to limit the invention.

FIGS. 1A-E illustrates an embodiment showing a method for detection of one or more components in a sample.

DETAILED DESCRIPTION OF THE INVENTION

The present invention relates to methods and reagents for use in the detection of a component in a sample on a solid support, comprising the use of a conjugate and polymer comprising metal particles of diameter in the nanometer range (i.e. between 0.1 and 500 nm) and a polymer. It further relates to methods and reagents for use in the detection of a component in a sample on a solid support, comprising the use of a streptavidin and optionally polymer bound to one or more supermagnetic particles. It further relates to methods and reagents for use in enhancing in vivo imaging and microscopy. It further relates to diagnostic kits.

In one aspect of the invention, one or more samples are immobilized onto the solid support, one or more probes applied thereto and the binding is detected. Thus, one embodiment of the present invention is a method for quantitatively and/or qualitatively detecting one or more components in a sample, each component capable of binding to a probe, comprising steps in the following order:
(a) applying one or more samples onto a solid support,
(b) contacting the solid support with one or more biotin-labeled probes,
(c) contacting the solid support with streptavidin-metal particle complex,
(d) contacting the solid support with conjugate comprising:
  one or more biotins,
  one or more polymers, and
  metal particles bound to said polymer,
(e) optionally contacting the solid support with metal enhancement reagent, and
(f) reading the solid support to quantitatively and/or qualitatively detect said component.

The inventors have found that when the signal of a specific interaction between probe and component is amplified using streptavidin-metal particle complex and the conjugate according to the invention, a sensitive and reproducible qualitative and/or quantitative indication of components is indicated.

According to one embodiment of the invention, step (a) above is preceded by the application of probe to the solid support. i.e.

(a0) applying one or more probes onto solid support,
(a) contacting solid support with one or more samples,
(b) contacting solid support with one or more biotin-labeled probes,
(c) contacting solid support with streptavidin-metal particle complex,
(d) contacting solid support with conjugate comprising:
  one or more biotins,
  one or more polymers, and
  metal particles bound to said polymer,
(e) optionally contacting solid support with metal enhancement reagent, and
(f) reading the solid support to quantitatively and/or qualitatively detect said component.

By applying probe to the solid support prior to the application of sample, sample is selectively bound to the solid support prior to the subsequent step, leading to reduced background signal. The probe of step (b) may be less selective than the probe of step (a0) and a still provide a superior signal to noise ratio. The probe of step (a0) may be the same or different from the probe of step (b). For example, the probe of step (a0) may be a monoclonal antibody and the probe of step (b) may be a polyclonal antibody.

In another aspect of the invention, one or more probes are immobilized onto the solid support and one or more samples applied thereto. Thus, another embodiment of the present invention is a method for quantitatively and/or qualitatively detecting one or more components in a sample, each component capable of binding to a probe, comprising steps in the following order:
(a) applying one or more probes onto solid support,
(b) contacting solid support with one or more biotin-labelled samples,
(c) contacting the solid support with streptavidin-metal particle complex,
(d) contacting the solid support with conjugate comprising:
  one or more biotins,
  one or more polymers, and
  metal particles bound to said polymer,
(e) optionally contacting the solid support with metal enhancement reagent, and
(f) reading the solid support to quantitatively and/or qualitatively detect said component.

By "applying" as used herein in reference to applying one or more samples or probes to a solid support, is meant deposition of one or more synthetic or biological substances on a solid support. The deposition may be by a manual method or by using a device, resulting in an action including, but not limited to spotting, pipetting, printing, jet printing, dropping etc.

The inventors have found that the nanometer scale and sometimes sub-nanometer scale of metal particle used in the steptavidin-metal particle complex and conjugate allows extremely high labelling indices. This provides enhanced detection sensitivity. Furthermore, a method according to the invention requires a minimum two contact steps, (c) and (d), so greatly reducing the time, the number of required reagents, and the possibility for error. The resulting change in colour not only permits evaluation with a scanning device but also with the naked eye, so obviating the need for optical or electronic detecting devices.

Furthermore, the inventors have found that using nanosized particles of metal according to the invention produces a variety of confinement effects which dramatically change the properties of the metal. Such properties appear to be altered when the entity or mechanism responsible for that property is confined within a space smaller than the critical length associated with that entity or mechanism. Some illustrations of such properties include but are not limited to electrical conductivity, dielectric constant, dielectric strength, dielectric loss, polarization, permitivity, critical current, superconductivity, piezoelectricity, mean free path, curie temperature, critical magnetic field, permeability, coercive force, magnetostriction, magnetoresistance, hall coefficient, BHmax, critical temperature, melting point, boiling point, sublimation point, phase transformation conditions, vapor pressure, anisotropy, adhesion, density, hardness, ductility, elasticity, porosity, strength, toughness, surface roughness, coefficient of thermal expansion, thermal conductivity, specific heat, latent heat, refractive index, absorptivity, emissivity, dispersivity, scattering, polarization, acidity, basicity, catalysis, reactivity, energy density, activation energy, free energy, entropy, frequency factor, environmental benigness, bioactivity, biocompatibility, and thermal and pressure coefficients of properties.

A "sample" represents at least a portion of an entity to be tested for the presence and/or concentration of one or more components. Samples may be derived from, for example, animals, plants, bacteria, viruses, micro-organisms, blood, blood components, other bodily fluids, tissues, cells, genome, proteome, drinking water, soil, domestic waste, industrial waste, any food stuff—liquid or solid, crops, biological preparations, biochemical preparations.

The biotin used to label a sample may be any type capable of binding to streptavidin, including mutations and portions. Methods of biotinylating a sample are described below.

By "solid support" herein is meant any solid support which is capable of immobilising components and/or samples. Such solid supports are known in the art and include, but are not limited to, nitrocellulose, glass slides, nylon, silane coated slides, nitrocellulose coated slides, plastics. A solid support may be capable of holding single spotted sample, multisamples and/or micro-arrays etc. A solid support preferably comprises nitrocellulose.

Consecutive application and contact steps such as steps (a0), (a), (b), (c) and (d) are preferably carried out so that at least part of the contact area of each step is the same. Contacting may effected at more than one separated points on a soild support. Contacting may also be achieved by covering a surface of a support with a single reagent. Contacting may also be achieved by a manual method or by using a device, resulting in an action including, but not limited to spotting, pipetting, printing, jet printing, dropping, soaking etc. According to an aspect of the invention, at least part of, and preferably most of the area of application or contact in steps (a0), (a), (b), (c) and (d), where applicable, is the same.

By "reading" as used herein means determining from the change in the properties of the solid support at the position where the sample or probe is applied, the concentration of the components i.e. a quantitative reading. By "reading" as used herein also means determining from the change in the properties of the solid support at the position where the sample or probe is applied, whether a component is present i.e. a qualitative reading. According to the invention a change in the property of the solid support may be a colour change (e.g. from white to red, from white to black, from white to grey) and/or a change in electrical conductivity and/or a change in magnetic field at the position where the sample or probe is applied. It is within the scope of the invention that a change in property may be read by surface plasmon resonance or ellipsometry.

Reading may mean using normal vision to detect a colour change on the solid support to determine the presence or absence of a component or to determine the concentration of a component. It is within the scope of the invention that the reading may be taken using a colour chart that allows a comparison of the colour of the sample with that of known concentrations of probe or component. It is within the scope of the invention that a colour change disclosed herein may be read with or without the aid of electronic and optical measuring equipment. For example, a colour change of the solid support may be read by means of a reflectance reader as discussed below.

Using a reflectance reader to measure a colour change leads to accurate measurements and allows the determination of the concentration of the probe or component. The concentration of an unknown component can be calculated by interpolation on a standard curve obtained with several concentrations of probe or component.

Reading may mean using an optical scanner to ascertain a colour change on the solid support to determine the presence or absence of a component or to determine the concentration of a component.

Reading may also mean using a device to measure a change of electrical conductivity or electrical current at the position on the solid support where the sample or probe is applied, to determine the concentration of the components. The inventors have found that the use of electrically-conducting metal particles in steps (c) and/or (d) according to the invention results in a change of electrical conductivity of the solid support. The change can be conveniently and accurately read using a device capable of detecting a change in conductivity and/or current across a solid support. Said device may comprise one or more of the following features: one or more electrical contact probes, circuitry to measure conductivity and/or current, an analogue to digital converter. According to one example, one probe of the device contacts an upper surface of the solid support at the position where the sample or probe is applied, and a second probe contacts the same position on the lower surface; the conductivity and/or current across said probes is measured by the device. According to another example, one probe of the device contacts an upper surface of the solid support at the position where the sample or probe is applied, and the whole of the lower surface of the solid support contacts a conducting plate; the conductivity and/or current across said probe and plate is measured by the device. The latter example has the convenience that the measurement of more than one sample requires movement of only the probe contacting the upper surface.

Reading may also mean using a device to measure a change of magnetic field at a position on the solid support where a sample or probe is applied, to determine the concentration of the components. The use of metal particles which are also magnetic in steps (c) and/or (d) according to the invention can result in a change of magnetic field of the solid support. The change can be conveniently and accurately read using a device capable of detecting a change in magnetic on a solid support. Said device may comprise one or more of the following features: one or more magnetic-field detecting probes, circuitry to measure magnetic fields, an analogue to digital converter. According to one example, a magnetic-field detecting probe of the device scans the surface of the solid support at the position where the sample or molecular probe is applied, and the magnetic-field of the solid support is measured by the device.

Reading may also mean using a device which utilises surface plasmon resonance to detect a change in surface properties on the solid support where a sample or probe is applied.

Reading may also mean using a device which detects a change in polarised light reflected from surface of the solid support where a sample or probe is applied. An example of such a device is an ellipsometer.

In Vivo Imaging

Another aspect of the present invention is a method for enhancing imaging by magnetic resonance of one or more components in a system, each component capable of binding to a probe comprising the steps of:

(i) adding a biotin-labelled probe to a system, (ii) adding streptavidin-metal particle complex to said system, and (iii) recording an image of the system using magnetic resonance imaging.

The inventors have found that the complexes formed using metal particles of a nanometer size or subnanometer size in step (ii), e.g. 0.8 m, have fundamentally different characteristics when compared with conjugates built around larger particles which make them suitable for use in enhancing in in vivo imaging. The small nanoparticles have a tight particle surface curvature which makes them less likely to attract a structured water dipole layer around it. Thus, the hydrodynamic radius is hence reduced. Also, these small metal particles carry less net negative charge, thus, they undergo less charge determined repulsion when approaching the sample surface. These characteristics appear to result in a better permeability in biological systems, organs and organisms. Furthermore, the nanoparticles of step (ii) are so small, they do not cause steric hinderance. This makes them ideal as markers for visualizing pathways, for example, of human metabolism.

A system according to the imaging embodiment of the invention may be a biological entity in which the presence and distribution of components is of interest. Examples of systems include humans, animals, plants, cells, tissues, organs, micro-organisms.

The method for enhancing the imaging of components in a system can be performed by a technician.

The method for enhancing the imaging of components in a system can be used to detect the susceptibility to medical conditions. The method for enhancing the imaging of components in a system can be used to detect the medical conditions which exists in a patient. Examples of components and conditions are provided in Table 1.

A "component" as used herein means any substance capable of binding to a probe enabling identification of said component. Examples of components include, but are not limited to DNA, cDNA, mRNA, RNA, nucleic acids, proteins, polypeptides, glycoproteins, receptors, ligands, signalling proteins, metabolites, toxins, cells, bacteria, viruses etc. Examples of components are provided in Table 1. Examples of types of components useful for detecting by imaging include receptors, cellular surface proteins, ribonucleic acids, desoxyribonucleic acids, cytoplasmic antigens, nuclear antigens, membrane antigens, hormones, metabolites, tumour antigens, mitochondrial proteins, mitochondrial DNA and mitochondrial RNA, nuclear proteins.

A "probe" as used herein means any compound capable of specific binding to a component. A nucleic acid oligomer binding to a gene, a ligand binding to a receptor, an antibody binding to an antigen are examples of probe/component interactions according to the invention. According to the present invention, the affinity of binding between a probe and a component is better than 10 µM, 5 µM, 2 µM, 1 µM, 0.1 uM, 0.01 uM or 1 nM. Examples of probes include but are not limited to nucleic acids, PNAs, proteins, peptides, antibodies, ligands, receptors etc.

The biotin used to label a probe may be any type capable of binding to streptavidin, including chemical variations thereof. Methods of biotinylating a probe are described below.

By "streptavidin-metal particle complex" as used herein is a complex comprising streptavidin and/or avidin and one or more metal particles. The streptavidin is any type of streptavidin capable of binding to biotin, including portions or mutations of streptavidin. The avidin is any type of avidin capable of binding to biotin, including portions or mutations of avidin. In one aspect of the invention, metal particles may be bound to streptavidin and/or avidin by non-covalent forces. In another aspect of the invention, metal particles may be bound to streptavidin and/or avidin by covalent bonding. Methods of providing streptavidin and/or avidin with one or more metal particles are known to the skilled person. The types of metal particle and their diameters are described in detail below.

A "conjugate" as used herein comprises one or more polymers labeled with one or more biotin molecules, and metal particles bound to said polymer. The biotin used to label a polymer may be any type capable of binding to streptavidin and/or avidin, including chemical variations thereof. According to one aspect of the invention, biotin is covalently attached to a polymer—methods therefor are described below. According to another aspect of the invention, the number of biotin molecules attached to a polymer may be less than 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000, and preferably in the range 1 to 500, 1 to 400, 1 to 300, 1 to 200, 1 to 100, and most preferably in the range 5 to 100.

A "polymer" as present in a conjugate according to the invention is any polymeric substance with a molecular weight greater than 500 Da, 1000 Da, 1500 Da, 2000 Da or 2500 Da, and most preferably greater than 500 Da. It is an aspect of the invention that a polymer exhibits no specific binding towards a sample or probe. It is an aspect of the invention that a polymer is biologically inert. In other words it has no specific binding towards other biological molecules, and other biological molecules do not specifically bind to it. It is an aspect of the invention that a polymer is capable of binding one or more metal particles by electrostatic or covalent interactions. The polymers which can be employed in the present invention may be chemically synthesized polymers or naturally occurring polymers. Examples of the chemically synthesized polymers include vinyl polymers, aramid polymers, polyvinylamine, poly(vinyl alcohol), poly(N-vinylcarbazole), poly(vinylpyridine), polypyrrole, polyphenyl polymers, poly(phenylene sulfide), poly(vinylidene fluoride), poly(methyl methacrylate), polymethylene polymers, polyimidazole, polyimide, polystyrene, olefin polymers, elastomers, engineering polymers, polyolfein, polyester, polycarbonate, engineering plastics, epoxy polymers, phenolic polymers, polyurethane, polydinene polymers, acrylic polymers, polyacrylamide, polyamide, polyacetal, polyether, polyacetylene, polyaniline, polyisobutylene, polyisoprene, poly(ethylene terephthalate), polyene polymers, poly(vinylidene chloride), poly(vinyl chloride), polycarbonate, poly(vinyl acetate), polypropylene, ethylene polymers, ion-exchange resins (e.g., Nafion), and silicone derivatives. Examples of the naturally occurring polymers include agarose, gellan gum, cellulose polymers (e.g., hydroxyethyl cellulose, hydroxypropyl cellulose, and carboxymethyl cellulose), dextran, dextrin, alginate salts, hyaluronate salts, poly(glutamic acid), poly(lysine), chitosan, lignin, carageenan, silk fibroin, agar, polypeptide, polypeptide, polysaccharide, polyethylene glycol, nucleic acid chain, peptic nucleic acid (PNA), polyglycoprotein, and gelatin. These polymers may also be derivatives thereof, copolymers obtained from one or more species selected from among the polymers and/or polymer derivatives, polymer-polymer complexes, polymer alloys, polymer blends, and polymer composites. A polymer may exhibit one or more of the above features. It is an aspect of the invention that a conjugate comprises essentially one polymer. It is another aspect of the invention that a conjugate comprises more than one polymer. It is an aspect of the invention that a polymer is albumin or dextran polymer.

In one aspect of the invention, metal particles may be bound to polymer by non-covalent forces. In another aspect of the invention, metal particles may be bound to polymer by covalent bonding. Methods of providing polymer one or more metal particles are known to the skilled person. The types of metal particle and their diameters are described in detail below.

According to an aspect of the invention, when a conjugate comprises more than one polymer, all the polymer molecules are the same (e.g. at least two molecules of albumin). Alternatively, when a conjugate may comprise more than one polymer, at least two polymers are different (e.g. one molecule of albumin, and one molecule of dextran).

According to another aspect of the invention, when a conjugate comprises more than one biotin, all the biotin molecules are the same (e.g. at least two molecules of biotin). Alternatively, when a conjugate may comprise more than one biotin, at least two biotins are different (e.g. one molecule of biotin, and one molecule of modified biotin).

The process of biotinylating a sample, probe or polymer is known to the skilled artisan and can be performed on proteins, peptides, nucleic acids or other compounds. For example, nucleic acid may be biotinylated by performing a polymerase chain reaction using biotinylated primer(s) specific for the sequence of interest. Peptides and proteins may be biotinylated using biotinylation reagents which, for example, biotinylate the C-terminus, the N-terminus and/or reactive side chains of the protein or peptide. Organic polymeric chains may be biotinylated using biotinylation reagents which, for example, target reactive side chains. Optionally, flexible linkers, such as alkyl chains, polynucleotide chains, polypeptide chains, etc. may in introduced between the biotin and the target. Such linkers may further enhance detection by reducing steric hinderance caused by the polypeptide. The present invention includes any method for the biotinylation of a sample, probe or polymer.

Metal Particles

The metal particles of the streptavidin-metal particle complex, or conjugate may be any which provide a colour change, a change in electrical conductance, a change in magnetic field, or improved contrast in in vivo imaging.

The particles suitable for use according to the invention include one or more of gold, silver, iron, nickel, gadolinium, lead, uranium, caesium, platinum, palladium, rhodium, technetium, tellurium, selenium, silicon (silicium), cupper, tin, rhenium, europium, aluminium, germanium, chromium, cadmium, niobium, titanium, magnesium, manganese, molybdenum, antimony, americium, lithium, wolfram, thallium, ruthenium, osmium, iridium, and/or metallic substances conducting or semi-conducting.

The transition metals that can be employed in the present invention encompass particles composed of any transition metal element species. Examples of the transition metals which can be employed include one or more of Sc, Y, La, Ac (scandium-group elements); Ti, Zr, Hf (titanium-group elements); V, Nb, Ta (vanadium-group elements); Cr, Mo, W (chromium-group elements); Mn, Tc, Re (manganese-group elements); Fe, Ru, Os (iron-group elements); Co, Rh, Ir (cobalt-group elements); Ni, Pd, Pt (nickel-group elements); Cu, Ag and Au (copper-group elements). Among these transition metal elements, noble metals such as platinum, palladium, rhodium, iridium, ruthenium, osmium, silver, and gold are preferred.

Examples of transition metals include noble metal complexes and organometallic compounds of noble metal. Specific examples include platinum complexes, palladium complexes, rhodium complexes, iridium complexes, ruthenium complexes, osmium complexes, silver complexes, gold complexes, and non-stoichiometric compounds thereof; and ions of a variety of noble metal complexes; e.g., alkyl complexes, aryl complexes, metallacycle complexes, carbene complexes, olefin complexes, arene complexes, eta-aryl complexes, cyclopentadienyl complexes, hydrido complexes, carbonyl complexes, oxo complexes, and nitrogen complexes.

It is an aspect of the invention that metal particles of the streptavidin-metal particle complex and conjugate are the same metal particle (e.g. both the complex of step (c) and the conjugate of step (d) comprise gold particles). It is an aspect of the invention that the metal particles of the streptavidin-metal particle complex and the metal particles of the conjugate are different (e.g. the complex of step (c) may comprise gold particles, the conjugate of step (d) may comprise silver particles). It is an aspect of the invention that the metal particles of the complex or conjugate is an heterologous mix of metal particles (e.g. the complex of step (c) may comprise a mixture of gold and silver particles).

According to one aspect of the invention, metal particles preferred for use in detecting components in a sample whereby a colour change is read include, but are not limited to one or more of gold, silver, palladium, rhodium, iridium, platinum, and nickel.

According to another aspect of the invention, metal particles preferred for use in detecting components in a sample whereby a change in electrical conductance is read include, but are not limited to one or more of gold, silver, iron, cupper, and nickel.

According to another aspect of the invention, metal particles preferred for use in detecting components in a sample whereby a change in magnetic field is read include, but are not limited to one or more of gold, silver, and iron.

According to another aspect of the invention, metal particles preferred for use in enhancing in vivo imaging according to the invention include, but are not limited to one or more of iron and gadolinium.

According to one aspect of the invention, metal particles may be of any average diameter in the nanometer or sub-nanometer range. In another aspect, the metal particles may have an average diameter of 0.6, 0.8 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm and 0.6 to 1.0 nm, 1.0 to 5.0 nm, 5.0 to 10 nm, 10 to 15 nm, 15 to 20 nm, 20 to 25 nm, 25 to 30 nm, 30 to 35 nm, 35 to 40 nm, and preferably 0.6 to 40 nm.

According to a preferred aspect of the invention, the streptavidin-metal particle complex or conjugate comprises one or more particles of gold with a diameter of 0.6 to 40 nm.

According to a preferred aspect of the invention, the streptavidin-metal particle complex, or conjugate comprises one or more particles of silver with a diameter of 0.6 to 40 nm.

According to a preferred aspect of the invention, the streptavidin-metal particle complex or conjugate comprises one or more particles of platinum with a diameter of 0.6 to 40 nm.

According to a preferred aspect of the invention, the streptavidin-metal particle complex or conjugate comprises one or more particles of palladium with a diameter of 0.6 to 40 nm.

The number of metal particles present in a complex or a conjugate may be less than 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000, and preferably in the range 5 to 50000, 5 to 100,000, to 500,000, 5 to 1,000,000.

The "metal enhancement reagent" of step (f) is any metal-containing reagent wherein the metal precipitates due to reduction. Examples include but are not limited to a silver enhancement reagent by Aurion (the Netherlands), BBI (UK), Sigma-Aldrich (USA), or Amersham (UK).

Superparamagnetic Particle

One aspect of the invention, the streptavidin metal-particle complex and/or the conjugate comprise superparamagnetic particles.

According to an aspect of the invention the streptavidin-metal particle complex in step (c) and/or the conjugate in step (d) comprise one or more superparamagnetic particles, and the solid support is read for any change in colour.

According to another aspect of the invention, the streptavidin-metal particle complex or conjugate comprise one or more superparamagnetic particles, and the solid support is read for any change in electrical conductivity or magnetic field.

According to another aspect of the invention, the streptavidin-metal particle complex in step (c) comprises one or more superparamagnetic particles, steps (d) and (e) are not performed, and the solid support is read for any change in electrical conductivity or magnetic field.

Since binding of a streptavidin-metal particle complex and optionally conjugate comprising superparamagnetic particles also leads a change in electrical conductivity, this characteristic can be conveniently measured using a reading device as mentioned above, without the need for precision optics. The use of such particles also leads to a change in the magnetic flux, which can be conveniently read by a reading device as mentioned above.

According to another aspect of the invention, streptavidin-metal particle complex in step (ii) comprises one or more superparamagnetic particles. A supermagnetic particle provides high sensitivity and contrast when used in magnetic resonance imaging.

Examples of superparamagnetic particles are known in the art and include, but are not limited to is iron, latex coated iron, iron oxide, and latex coated iron oxide.

According to another aspect of the invention, a superparamagnetic particle has a magnetic susceptibility of in the range 1 to 100 emu/g, 10 to 80 emu/g, 10 to 70 emu/g, 10 to 50 emu/g, 20 to 50 emu/g and preferably approximately 40 emu/g.

According to another aspect of the invention, a superparamagnetic particle has an iron oxide content of in the range 10 to 80%, 20 to 80%, 30 to 80%, 40 to 80%, 50 to 80%, 60 to 80%, 70 to 80%, 10 to 70%, 20 to 70%, 30 to 70%, 40 to 70%, 50 to 70%, 60 to 70%, and preferably approximately 70%.

According to one aspect of the invention, the diameter of a superparamagnetic particle is between 50 and 400 nm, 50 and 300 nm, 50 and 200 nm, 50 and 100 nm, 100 and 400 nm, 100 and 300 nm, 100 and 200 nm, 200 and 400 nm, 200 and 300 nm, 150 and 250 nm, and is preferably 200 nm.

According to one aspect of the invention, the number of superparamagnetic particles in the strepavidin-metal particle complex, or in the conjugate may be less than 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000, and preferably in the range 5 to 50000, 5 to 100,000, to 500,000, 5 to 1,000,000.

In another aspect of the invention, superparamagnetic particles are bound to streptavidin (or avidin) or polymer using electrostatic interactions. In another aspect of the invention, superparamagnetic particles are covalently bound to streptavidin (or avidin) or polymer.

Pretreatment

In one aspect of the invention, sample or probe is applied to the solid support without the addition of any extra reagents to the sample or probe prior to application. In another aspect of the invention, sample or probe is applied to the solid support after a preconditioning procedure which increases the concentration of salt in said samples. The salt may be any dissociating salt in the art, including, but not limited to sodium chloride, potassium chloride. The preconditioning may comprise the addition of a volume of salt solution of a known concentration to a volume of sample or probe. The preconditioning step may comprise the addition of a volume of salt solution of a known concentration to an unknown volume of sample or probe. The concentration of salt in the sample may be adjusted to lie in the range of 100 mM to 500 mM, 500 mM to 1 M, 1 M to 1.5 M, 1.5 M to 2 M, 2 M to 2.5 M, 2.5 M to 3 M, 3 M to 3.5 M, 3.5 M to 4 M, 3.5 M to 5 M, 0.5 M to 2.5 M, 0.5 M to 3 M, or 0.5 M to 4 M.

Drying

In another aspect of the invention, after the applying step in (a) the samples or probes are not dried or baked before step (b) is performed. In another aspect of the invention, the samples or probes applied to the solid support in step (a) are allowed to dry. Similarly, step (a0) may be followed by step (a) in the absence or presence of an intervening drying step. Methods of drying are known in the art and can include, but are not limited to, drying in the air, drying in a incubator, drying in a chamber under low pressure with optionally heating. According to another aspect of the invention, the samples or probes applied to the solid support are baked by exposed to a temperature of between 60 to 70 degrees Celsius, 65 to 75 degrees Celsius, 70 to 80 degrees Celsius, 75 to 85 degrees Celsius, 80 to 90 degrees Celsius, 65 degrees Celsius, 70 degrees Celsius, 75 degrees Celsius, 80 degrees Celsius, 85 degrees Celsius or 90 degrees Celsius. The exposure time may be for no more than 10 minutes, 15 minutes, 20 minutes, 25 minutes, 30 minutes, 35 minutes, 40 minutes, 45 minutes, 50 minutes, 55 minutes or 60 minutes. The samples or probes may be dried and then baked, only dried, only baked.

Storage

In another aspect of the invention, after the applying step in (a) or (a0), the solid support is stored. The temperature at which the solid support on which sample or probe has been applied is stored may be between 0 and 10 degrees Celsius, 2 and 10 degrees, 3 and 10 degrees Celsius, 4 and 10 degrees Celsius, 5 and 10 degrees Celsius, 6 and 10 degrees Celsius, 7 and 10 degrees Celsius, 0 and 5 degrees Celsius, 1 and 5 degrees Celsius, 2 and 5 degrees Celsius, 3 and 5 degrees Celsius, 1 degree Celsius, 2 degrees Celsius, 3 degrees Celsius, 4 degrees Celsius, 5 degrees Celsius, 6 degrees Celsius, 7 degrees Celsius, 8 degrees Celsius, 9 degrees Celsius, 10 degrees Celsius.

Wash Steps

The introduction of wash steps in the method above, may be determined by the skilled artisan in accordance with commonly understood protocols in immunoassays such as ELISA and Western blots. For example, one or more wash steps may be introduced after one or more contacting steps, using with a washing reagent such as a buffer. For example, washes may be performed after steps (a0), (b), (c), (d), and (e), where applicable. Preferably, a wash is performed after every step. Examples of buffers include physiological solution, phosphate buffer saline (PBS), TRIS-buffer, SSC-buffer, SSPE-buffer, and buffers in which a non-specific binding protein is added to reduce aspecific binding of reactive components.

Pre-Applied Probe Solid Supports

As described in some embodiments above, one or more probes may be applied to a solid support prior to the application of sample. According to one embodiment of the present invention, a solid support is provided with probe pre-applied. In one aspect of the invention, the solid support with probe pre-applied is provided with probe located at one or more positions, said probe recognising the same component. In one aspect of the invention, the solid support with probepre-applied is provided with probe located one or more positions, said probe recognising different components. A method in which the solid support is provided with probe pre-applied enables a sample to be assayed for components without the necessity for performing probe application steps. Furthermore, a method using a solid support with probe pre-applied, and probe recognising more than one component, enables single samples to be analysed for several components with a single incubation. For example, a single solid support may be used to detect several cancerous or pre-cancerous conditions by screening a single sample.

It is one advantage of the invention that it does not necessarily require an optical reading device such as a laser scanner or back-scatter measuring equipment, and hence is convenient for use in environments away from laboratory conditions. The invention allows quantitative and/or qualitative results to be obtained at the location at which the sample was taken, for example, in a general practitioner's surgery, in an individual's home, in hospitals, generally 'in the field' without any specialist analytical instruments. Furthermore, the invention provides an assay that is as sensitive as, or, more sensitive than assays which use fluorescence. Furthermore, since specialised measuring equipment is not necessarily required, the assay could be performed by a non-specialist.

Kit

Another aspect of the present invention is a kit for the quantitative and/or qualitative detection of components in a sample comprising streptavidin-metal particle complex.

Such a kit allows a quantitative and/or qualitative detection of components on a solid support, and/or a detection of components in a system by magnetic resonance.

A kit according to the present invention allows a skilled artisan to perform one or more steps of a method disclosed herein, in a convenient manner. The kit may allow a method of the present invention to be performed without the need to measure or determine the concentrations of reagents, so enabling a fast and reproducible assaying of one or more samples.

Another aspect of the present invention is a kit for the quantitative and/or qualitative detection of components in a sample further comprising one or more solid supports Another aspect of the present invention is a kit as described above, comprising a solid support, wherein said support is pre-loaded with one or more probes. In one aspect of the invention, the solid support is provided with probe located one or more positions, said probe recognising the same component. In one aspect of the invention, the solid support is provided with probe located one or more positions, said probe recognising different components. In another aspect of the invention, the solid support is provided with one or more probes which are capable of binding to the components listed in Table 1. Thus, a kit supplied with solid support in which the molecular probe is pre-applied enables a sample to be assayed for components without the necessity for performing application steps. Furthermore, a kit supplied with solid support pre-spotted with more than one molecule probe, each capable of recognising a different component enables a single sample to be analysed for several components with a single incubation. For example, a single solid support may be used to detect for several pre-cancerous or cancerous conditions as described below by screening a single sample.

Another aspect of the present invention is a kit for the quantitative and/or qualitative detection of components in a sample further comprising conjugate.

Another aspect of the present invention is a kit for the detection of components in a sample as disclosed herein, further comprising one or more biotin-labelled probes. Each probe may be specific for a component in a sample to be detected.

Another aspect of the present invention is a kit for the detection of components in a sample as disclosed herein further comprising metal enhancement reagent. According to one aspect of the invention, metal enhancement reagent is present in one or more containers. Examples of containers according to the invention are indicated above.

Another aspect of the present invention is a kit for the detection of components in a sample as disclosed herein as disclosed herein, further comprising reagent for the bioinylation of probes or sample to be tested. As already mentioned above, method and reagent for biotinylation of probes and sample are known in the art.

According to one aspect of the invention, complex, conjugate and/or reagents for biotinylation are present in separate containers. According to the invention a container may be any sealed or resealable vessel suitable for carrying a quantity of complex, conjugate and/or reagents for biotinylation. Examples include, but are not limited to screw cap vials, push cap vials, break-seal-to-open vials, syringes.

In another aspect of the invention, the kit comprises one or more additional parts to enable the skilled person to perform one or more of the method steps disclosed herein. The kit may comprise one or more additional reagents enabling the skilled person to perform the complete method. Alternatively, the kit may comprise a minimum number of parts, such as only streptavidin metal-particle complex, for example, that enables a skilled person to perform the method disclosed herein. A kit according to the invention may comprise any combination of parts or reagents disclosed herein to enable a skilled person to perform a method disclosed herein.

In another aspect of the invention, the kit contains instructions for use. In another aspect of the invention the instructions describing a method of the invention as disclosed herein.

In another aspect of the invention, the kit may be used for the diagnosis of disease, susceptibility of disease, monitoring the progress of disease, monitoring the progress of disease during treatment, testing of food, water, soil, testing for contamination, testing for the presence of genetically modified (GM) food components and/or organisms.

Detection of Conditions

Another aspect of the present invention is a method and/or kit as disclosed herein for detecting the presence of a component in a sample, wherein the sample to be tested may comprise one or more components related to a disease. Another aspect of the present invention is a method and/or kit as disclosed herein for imaging components in a system by magnetic resonance, wherein the system may comprise one or more components related to a disease. According to one embodiment, a probe is an antibody directed against the DNA, mRNA, cDNA or polypeptide representing said component or part thereof in the diseased individual. Alternatively, a probe is a nucleic acid (e.g. DNA, PNA, RNA) oligomer which is capable of hybridizing to the DNA, mRNA, and/or cDNA representing said component or part thereof in the diseased individual. A method and/or kit of the invention uses one or more of the embodiments disclosed herein. Examples of components which are associated with diseases and which are detectable using the method and/or kit of the invention by way of one or more probes directed there to are provided in Table 1.

A method and/or kit according to the present invention may be used for the diagnosis and detection of cancer in individuals, for example, for the diagnosis of a type of cancer, for the early detection of cancer, to monitor the progress of cancer in individuals already diagnosed with the disease, to detect a relapse of cancer. Cancer is still a major disease and to prolong life expectancy, it would be advantageous to detect the disease in a pre-clinical stage. A diagnostic assay as disclosed herein makes this possible. Non-limiting examples of components to which cancer or several hereditary conditions are associated with are provided in Table 1 and, one or more of which are detectable using the method and/or kit of the invention. A diagnosis may require detection of one of more of the listed molecules.

TABLE 1

List of components which are disease-related and are detectable using the kit and/or method of the present invention.

| Number | Component | Comments |
|---|---|---|
| 1. | BRCA1 | breast cancer 1, early onset |
| 2. | TP53 | tumor protein p53 (Li-Fraumeni syndrome) |
| 3. | CFTR | cystic fibrosis transmembrane conductance regulator, ATP-binding cassette (sub-family C, member 7) |
| 4. | APP | amyloid beta (A4) precursor protein (protease nexin-II, Alzheimer disease) |
| 5. | APOE | apolipoprotein E |
| 6. | BRCA2 | breast cancer 2, early onset |
| 7. | HBB | hemoglobin, beta |
| 8. | APC | adenomatosis polyposis coli |
| 9. | MYC | v-myc myelocytomatosis viral oncogene homolog (avian) |
| 10. | HD | huntington (Huntington disease) |
| 11. | BCL2 | B-cell CLL/lymphoma 2 |
| 12. | ABL1 | v-abl Abelson murine leukemia viral oncogene homolog 1 |
| 13. | BAX | BCL2-associated X protein |

TABLE 1-continued

List of components which are disease-related and are detectable using the kit and/or method of the present invention.

| Number | Component | Comments |
|---|---|---|
| 14. | DMD | dystrophin (muscular dystrophy, Duchenne and Becker types), includes DXS142, DXS164, DXS206, DXS230, DXS239, DXS268, DXS269, DXS270, DXS272 |
| 15. | CDKN2A | cyclin-dependent kinase inhibitor 2A (melanoma, p16, inhibits CDK4) |
| 16. | ATM | ataxia telangiectasia mutated (includes complementation groups A, C and D) |
| 17. | TNF | tumor necrosis factor (TNF superfamily, member 2) |
| 18. | RB1 | retinoblastoma 1 (including osteosarcoma) |
| 19. | VEGF | vascular endothelial growth factor |
| 20. | ERBB2 | v-erb-b2 erythroblastic leukemia viral oncogene homolog 2, neuro/glioblastoma derived oncogene homolog (avian) |
| 21. | FGG | fibrinogen, gamma polypeptide |
| 22. | HPRT1 | hypoxanthine phosphoribosyltransferase 1 (Lesch-Nyhan syndrome) |
| 23. | MAPT | microtubule-associated protein tau |
| 24. | MDM2 | Mdm2, transformed 3T3 cell double minute 2, p53 binding protein (mouse) |
| 25. | RUNX1 | runt-related transcription factor 1 (acute myeloid leukemia 1; aml1 oncogene) |
| 26. | SOD1 | superoxide dismutase 1, soluble (amyotrophic lateral sclerosis 1 (adult)) |
| 27. | CDKN1A | cyclin-dependent kinase inhibitor 1A (p21, Cip1) |
| 28. | PAX6 | paired box gene 6 (aniridia, keratitis) |
| 29. | NF1 | neurofibromin 1 (neurofibromatosis, von Recklinghausen disease, Watson disease) |
| 30. | FN1 | fibronectin 1 |
| 31. | CASP3 | caspase 3, apoptosis-related cysteine protease |
| 32. | PAH | phenylalanine hydroxylase |
| 33. | GAPD | glyceraldehyde-3-phosphate dehydrogenase |
| 34. | PTEN | phosphatase and tensin homolog (mutated in multiple advanced cancers 1) |
| 35. | HFE | hemochromatosis |
| 36. | FGFR3 | fibroblast growth factor receptor 3 (achondroplasia, thanatophoric dwarfism) |
| 37. | EGFR | epidermal growth factor receptor (erythroblastic leukemia viral (v-erb-b) oncogene homolog, avian) |
| 38. | DSCR1 | Down syndrome critical region gene 1 |
| 39. | MLH1 | mutL homolog 1, colon cancer, nonpolyposis type 2 (*E. coli*) |
| 40. | PABPC1 | poly(A) binding protein, cytoplasmic 1 |
| 41. | CYP3A5 | cytochrome P450, subfamily IIIA (niphedipine oxidase), polypeptide 5 |
| 42. | PSEN1 | presenilin 1 (Alzheimer disease 3) |
| 43. | FBN1 | fibrillin 1 (Marfan syndrome) |
| 44. | MSH2 | mutS homolog 2, colon cancer, nonpolyposis type 1 (*E. coli*) |
| 45. | AKT1 | v-akt murine thymoma viral oncogene homolog 1 |
| 46. | CCND1 | cyclin D1 (PRAD1: parathyroid adenomatosis 1) |
| 47. | MTHFR | 5,10-methylenetetrahydrofolate reductase (NADPH) |
| 48. | AR | androgen receptor (dihydrotestosterone receptor; testicular feminization; spinal and bulbar muscular atrophy; Kennedy disease) |
| 49. | TGFB1 | transforming growth factor, beta 1 (Camurati-Engelmann disease) |
| 50. | IL6 | interleukin 6 (interferon, beta 2) |
| 51. | KRAS2 | v-Ki-ras2 Kirsten rat sarcoma 2 viral oncogene homolog |
| 52. | HRAS | v-Ha-ras Harvey rat sarcoma viral oncogene homolog |
| 53. | RET | ret proto-oncogene (multiple endocrine neoplasia and medullary thyroid carcinoma 1, Hirschsprung disease) |
| 54. | PPARG | peroxisome proliferative activated receptor, gamma |
| 55. | ACTB | actin, beta |
| 56. | CDH1 | cadherin 1, type 1, E-cadherin (epithelial) |
| 57. | ESR1 | estrogen receptor 1 |
| 58. | IGF1 | insulin-like growth factor 1 (somatomedin C) |
| 59. | GSTP1 | glutathione S-transferase pi |
| 60. | IL8 | interleukin 8 |
| 61. | LPL | lipoprotein lipase |
| 62. | FMR1 | fragile X mental retardation 1 |
| 63. | WT1 | Wilms tumor 1 |
| 64. | IL1B | interleukin 1, beta |
| 65. | CYP1A1 | cytochrome P450, subfamily I (aromatic compound-inducible), polypeptide 1 |
| 66. | CTNNB1 | catenin (cadherin-associated protein), beta 1 (88 kD) |
| 67. | ITGA5 | integrin, alpha 5 (fibronectin receptor, alpha polypeptide) |
| 68. | FOS | v-fos FBJ murine osteosarcoma viral oncogene homolog |

TABLE 1-continued

List of components which are disease-related and are detectable using the kit and/or method of the present invention.

| Number | Component | Comments |
|---|---|---|
| 69. | KIT | v-kit Hardy-Zuckerman 4 feline sarcoma viral oncogene homolog |
| 70. | ATP7B | ATPase, Cu++ transporting, beta polypeptide (Wilson disease) |
| 71. | IGF2 | insulin-like growth factor 2 (somatomedin A) |
| 72. | JUN | v-jun sarcoma virus 17 oncogene homolog (avian) |
| 73. | CYP2C19 | cytochrome P450, subfamily IIC (mephenytoin 4-hydroxylase), polypeptide 19 |
| 74. | BCR | breakpoint cluster region |
| 75. | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 76. | CASP8 | caspase 8, apoptosis-related cysteine protease |
| 77. | INSR | insulin receptor |
| 78. | G6PD | glucose-6-phosphate dehydrogenase |
| 79. | IL4 | interleukin 4 |
| 80. | DRD2 | dopamine receptor D2 |
| 81. | FGFR1 | fibroblast growth factor receptor 1 (fms-related tyrosine kinase 2, Pfeiffer syndrome) |
| 82. | COL1A1 | collagen, type I, alpha 1 |
| 83. | BLM | Bloom syndrome |
| 84. | NF2 | neurofibromin 2 (bilateral acoustic neuroma) |
| 85. | MMP1 | matrix metalloproteinase 1 (interstitial collagenase) |
| 86. | IL2 | interleukin 2 |
| 87. | GRB2 | growth factor receptor-bound protein 2 |
| 88. | BCL2L1 | BCL2-like 1 |
| 89. | PSEN2 | presenilin 2 (Alzheimer disease 4) |
| 90. | TNFRSF6 | tumor necrosis factor receptor superfamily, member 6 |
| 91. | CD44 | CD44 antigen (homing function and Indian blood group system) |
| 92. | MMP9 | matrix metalloproteinase 9 (gelatinase B, 92 kD gelatinase, 92 kD type IV collagenase) |
| 93. | ABCB1 | ATP-binding cassette, sub-family B (MDR/TAP), member 1 |
| 94. | GSTM1 | glutathione S-transferase M1 |
| 95. | IL1A | interleukin 1, alpha |
| 96. | MET | met proto-oncogene (hepatocyte growth factor receptor) |
| 97. | ABO | ABO blood group (transferase A, alpha 1-3-N-acetylgalactosaminyltransferase; transferase B, alpha 1-3-galactosyltransferase) |
| 98. | NRAS | neuroblastoma RAS viral (v-ras) oncogene homolog |
| 99. | NAT2 | N-acetyltransferase 2 (arylamine N-acetyltransferase) |
| 100. | EGR1 | early growth response 1 |
| 101. | TTR | transthyretin (prealbumin, amyloidosis type I) |
| 102. | SOD2 | superoxide dismutase 2, mitochondrial |
| 103. | SCYA2 | small inducible cytokine A2 (monocyte chemotactic protein 1) |
| 104. | NOS3 | nitric oxide synthase 3 (endothelial cell) |
| 105. | CDC2 | cell division cycle 2, G1 to S and G2 to M |
| 106. | STAT1 | signal transducer and activator of transcription 1, 91 kD |
| 107. | SNCA | synuclein, alpha (non A4 component of amyloid precursor) |
| 108. | CLU | clusterin (complement lysis inhibitor, SP-40,40, sulfated glycoprotein 2, testosterone-repressed prostate message 2, apolipoprotein J) |
| 109. | CDKN1B | cyclin-dependent kinase inhibitor 1B (p27, Kip1) |
| 110. | TYR | tyrosinase (oculocutaneous albinism IA) |
| 111. | MADH4 | MAD, mothers against decapentaplegic homolog 4 (Drosophila) |
| 112. | CDK2 | cyclin-dependent kinase 2 |
| 113. | MMP3 | matrix metalloproteinase 3 (stromelysin 1, progelatinase) |
| 114. | YWHAZ | tyrosine 3-monooxygenase/tryptophan 5-monooxygenase activation protein, zeta polypeptide |
| 115. | CASP1 | caspase 1, apoptosis-related cysteine protease (interleukin 1, beta, convertase) |
| 116. | PCNA | proliferating cell nuclear antigen |
| 117. | HLA-A, -B, -C | major histocompatibility complex, class I, A, B, C |
| 118. | APOB | apolipoprotein B (including Ag(x) antigen) |
| 119. | CASP9 | caspase 9, apoptosis-related cysteine protease |
| 120. | NOS2A | nitric oxide synthase 2A (inducible, hepatocytes) |
| 121. | IFNG | interferon, gamma |
| 122. | APOA1 | apolipoprotein A-I |
| 123. | AGT | angiotensinogen (serine (or cysteine) proteinase inhibitor, clade A (alpha-1 antiproteinase, antitrypsin), member 8) |

TABLE 1-continued

List of components which are disease-related and are detectable using the
kit and/or method of the present invention.

| Number | Component | Comments |
| --- | --- | --- |
| 124. | ADA | adenosine deaminase |
| 125. | ICAM1 | intercellular adhesion molecule 1 (CD54), human rhinovirus receptor |
| 126. | CYP19 | cytochrome P450, subfamily XIX (aromatization of androgens) |
| 127. | SLC6A4 | solute carrier family 6 (neurotransmitter transporter, serotonin), member 4 |
| 128. | TNFRSF1A | tumor necrosis factor receptor superfamily, member 1A |
| 129. | CD4 | CD4 antigen (p55) |
| 130. | VWF | von Willebrand factor |
| 131. | ACTA1 | actin, alpha 1, skeletal muscle |
| 132. | MECP2 | methyl CpG binding protein 2 (Rett syndrome) |
| 133. | COMT | catechol-O-methyltransferase |
| 134. | TERT | telomerase reverse transcriptase |
| 135. | PKD | polycystic kidney disease 1 (autosomal dominant) |
| 136. | F7 | coagulation factor VII (serum prothrombin conversion accelerator) |
| 137. | PMP22 | peripheral myelin protein 22 |
| 138. | F5 | coagulation factor V (proaccelerin, labile factor) |
| 139. | PPARA | peroxisome proliferative activated receptor, alpha |
| 140. | GCK | glucokinase (hexokinase 4, maturity onset diabetes of the young 2) |
| 141. | MUC1 | mucin 1, transmembrane |
| 142. | SPP1 | secreted phosphoprotein 1 (osteopontin, bone sialoprotein I, early T-lymphocyte activation 1) |
| 143. | RAF1 | v-raf-1 murine leukemia viral oncogene homolog 1 |
| 144. | IGF1R | insulin-like growth factor 1 receptor |
| 145. | IL4R | interleukin 4 receptor |
| 146. | DCC | deleted in colorectal carcinoma |
| 147. | PML | promyelocytic leukemia |
| 148. | PDGFRB | platelet-derived growth factor receptor, beta polypeptide |
| 149. | AGTR1 | angiotensin receptor 1 |
| 150. | UBE3A | ubiquitin protein ligase E3A (human papilloma virus E6-associated protein, Angelman syndrome) |
| 151. | CREBBP | CREB binding protein (Rubinstein-Taybi syndrome) |
| 152. | CYP1B1 | cytochrome P450, subfamily I (dioxin-inducible), polypeptide 1 (glaucoma 3, primary infantile) |
| 153. | AKT2 | v-akt murine thymoma viral oncogene homolog 2 |
| 154. | PLAT | plasminogen activator, tissue |
| 155. | CHRNA7 | cholinergic receptor, nicotinic, alpha polypeptide 7 |
| 156. | TIMP1 | tissue inhibitor of metalloproteinase 1 (erythroid potentiating activity, collagenase inhibitor) |
| 157. | NFKB1 | nuclear factor of kappa light polypeptide gene enhancer in B-cells 1 (p105) |
| 158. | STAT3 | signal transducer and activator of transcription 3 (acute-phase response factor) |
| 159. | CDC42 | cell division cycle 42 (GTP binding protein, 25 kD) |
| 160. | VDR | vitamin D (1,25-dihydroxyvitamin D3) receptor |
| 161. | NTRK1 | neurotrophic tyrosine kinase, receptor, type 1 |
| 162. | VIM | vimentin |
| 163. | TGFBR2 | transforming growth factor, beta receptor II (70-80 kD) |
| 164. | DHFR | dihydrofolate reductase |
| 165. | PTCH | patched homolog (*Drosophila*) |
| 166. | CYP2A6 | cytochrome P450, subfamily IIA (phenobarbital-inducible), polypeptide 6 |
| 167. | HSPCA | heat shock 90 kD protein 1, alpha |
| 168. | E2F1 | E2F transcription factor 1 |
| 169. | CACNA1A | calcium channel, voltage-dependent, P/Q type, alpha 1A subunit |
| 170. | LCK | lymphocyte-specific protein tyrosine kinase |
| 171. | LGALS3 | lectin, galactoside-binding, soluble, 3 (galectin 3) |
| 172. | RARA | retinoic acid receptor, alpha |
| 173. | PDZK1 | PDZ domain containing 1 |
| 174. | ALDH2 | aldehyde dehydrogenase 2 family (mitochondrial) |
| 175. | PAX3 | paired box gene 3 (Waardenburg syndrome 1) |
| 176. | FGF2 | fibroblast growth factor 2 (basic) |
| 177. | GJB1 | gap junction protein, beta 1, 32 kD (connexin 32, Charcot-Marie-Tooth neuropathy, X-linked) |
| 178. | LMNA | lamin A/C |
| 179. | CAPN3 | calpain 3, (p94) |
| 180. | ADPRT | ADP-ribosyltransferase (NAD+; poly (ADP-ribose) polymerase) |
| 181. | TUBB | tubulin, beta polypeptide |
| 182. | ABCA1 | ATP-binding cassette, sub-family A (ABC1), member 1 |
| 183. | IL1RN | interleukin 1 receptor antagonist |

TABLE 1-continued

List of components which are disease-related and are detectable using the kit and/or method of the present invention.

| Number | Component | Comments |
|---|---|---|
| 184. | CTGF | connective tissue growth factor |
| 185. | GSTT1 | glutathione S-transferase theta 1 |
| 186. | DRD4 | dopamine receptor D4 |
| 187. | HTR2A | 5-hydroxytryptamine (serotonin) receptor 2A |
| 188. | FHIT | fragile histidine triad gene |
| 189. | ETV6 | ets variant gene 6 (TEL oncogene) |
| 190. | PDGFB | platelet-derived growth factor beta polypeptide (simian sarcoma viral (v-sis) oncogene homolog) |
| 191. | PPP3R1 | protein phosphatase 3 (formerly 2B), regulatory subunit B (19 kD), alpha isoform (calcineurin B, type I) |
| 192. | TIMP3 | tissue inhibitor of metalloproteinase 3 (Sorsby fundus dystrophy, pseudoinflammatory) |
| 193. | COL1A2 | collagen, type I, alpha 2 |
| 194. | ITGB3 | integrin, beta 3 (platelet glycoprotein IIIa, antigen CD61) |
| 195. | COL3A1 | collagen, type III, alpha 1 (Ehlers-Danlos syndrome type IV, autosomal dominant) |
| 196. | ESR2 | estrogen receptor 2 (ER beta) |
| 197. | B2M | beta-2-microglobulin |
| 198. | SDF1 | stromal cell-derived factor 1 |
| 199. | F9 | coagulation factor IX (plasma thromboplastic component, Christmas disease, hemophilia B) |
| 200. | MAPK14 | mitogen-activated protein kinase 14 |
| 201. | BAK1 | BCL2-antagonist/killer 1 |
| 202. | ITGB1 | integrin, beta 1 (fibronectin receptor, beta polypeptide, antigen CD29 includes MDF2, MSK12) |
| 203. | ACTG1 | actin, gamma 1 |
| 204. | KDR | kinase insert domain receptor (a type III receptor tyrosine kinase) |
| 205. | SCTR | secretin receptor |
| 206. | LEPR | leptin receptor |
| 207. | SP1 | Sp1 transcription factor |
| 208. | CDKN1C | cyclin-dependent kinase inhibitor 1C (p57, Kip2) |
| 209. | MYCN | v-myc myelocytomatosis viral related oncogene, neuroblastoma derived (avian) |
| 210. | IiIL12B | interleukin 12B (natural killer cell stimulatory factor 2, cytotoxic lymphocyte maturation factor 2, p40) |
| 211. | IGF2R | insulin-like growth factor 2 receptor |
| 212. | FLT1 | fms-related tyrosine kinase 1 (vascular endothelial growth factor/vascular permeability factor receptor) |
| 213. | CD36 | CD36 antigen (collagen type I receptor, thrombospondin receptor) |
| 214. | FRD | Friedreich ataxia |
| 215. | COL2A1 | collagen, type II, alpha 1 (primary osteoarthritis, spondyloepiphyseal dysplasia, congenital) |
| 216. | GSN | gelsolin (amyloidosis, Finnish type) |
| 217. | CYP2E | cytochrome P450, subfamily IIE (ethanol-inducible) |
| 218. | APAF1 | apoptotic protease activating factor |
| 219. | ANK1 | ankyrin 1, erythrocytic |
| 220. | SLC6A3 | solute carrier family 6 (neurotransmitter transporter, dopamine), member 3 |
| 221. | CASP7 | caspase 7, apoptosis-related cysteine protease |
| 222. | MYH7 | myosin, heavy polypeptide 7, cardiac muscle, beta |
| 223. | JUNB | jun B proto-oncogene |
| 224. | GHR | growth hormone receptor |
| 225. | IRS1 | insulin receptor substrate 1 |
| 226. | CASP10 | caspase 10, apoptosis-related cysteine protease |
| 227. | BDNF | brain-derived neurotrophic factor |
| 228. | ATP7A | ATPase, Cu++ transporting, alpha polypeptide (Menkes syndrome) |
| 229. | TCF1 | transcription factor 1, hepatic; LF-B1, hepatic nuclear factor (HNF1), albumin proximal factor |
| 230. | HGF | hepatocyte growth factor (hepapoietin A; scatter factor) |
| 231. | CYP17 | cytochrome P450, subfamily XVII (steroid 17-alpha-hydroxylase), adrenal hyperplasia |
| 232. | PTPN1 | protein tyrosine phosphatase, non-receptor type 1 |
| 233. | ADRB3 | adrenergic, beta-3-, receptor |
| 234. | TNFSF6 | tumor necrosis factor (ligand) superfamily, member 6 |
| 235. | ERCC5 | excision repair cross-complementing rodent repair deficiency, complementation group 5 (xeroderma pigmentosum, complementation group G (Cockayne syndrome)) |
| 236. | VCAM1 | vascular cell adhesion molecule 1 |
| 237. | TF | transferrin |

TABLE 1-continued

List of components which are disease-related and are detectable using the
kit and/or method of the present invention.

| Number | Component | Comments |
|---|---|---|
| 238. | ACE | angiotensin I converting enzyme (peptidyl-dipeptidase A) 1 |
| 239. | LRP1 | low density lipoprotein-related protein 1 (alpha-2-macroglobulin receptor) |
| 240. | CDK5 | cyclin-dependent kinase 5 |
| 241. | ACACA | acetyl-Coenzyme A carboxylase alpha |
| 242. | TNFRSF1B | tumor necrosis factor receptor superfamily, member 1B |
| 243. | NOTCH3 | Notch homolog 3 (*Drosophila*) |
| 244. | ERBB3 | v-erb-b2 erythroblastic leukemia viral oncogene homolog 3 (avian) |
| 245. | CSK | c-src tyrosine kinase |
| 246. | SCN5A | sodium channel, voltage-gated, type V, alpha polypeptide (long (electrocardiographic) QT syndrome 3) |
| 247. | BCL6 | B-cell CLL/lymphoma 6 (zinc finger protein 51) |
| 248. | FYN | FYN oncogene related to SRC, FGR, YES |
| 249. | CTSK | cathepsin K (pycnodysostosis) |
| 250. | SPARC | secreted protein, acidic, cysteine-rich (osteonectin) |
| 251. | NFKB2 | nuclear factor of kappa light polypeptide gene enhancer in B-cells 2 (p49/p100) |
| 252. | SCYA5 | small inducible cytokine A5 (RANTES) |
| 253. | BMP4 | bone morphogenetic protein 4 |
| 254. | ATP2A2 | ATPase, Ca++ transporting, cardiac muscle, slow twitch 2 |
| 255. | NR3C1 | nuclear receptor subfamily 3, group C, member 1 |
| 256. | THBS1 | thrombospondin 1 |
| 257. | CETP | cholesteryl ester transfer protein, plasma |
| 258. | PTPRC | protein tyrosine phosphatase, receptor type, C |
| 259. | NME1 | non-metastatic cells 1, protein (NM23A) expressed in |
| 260. | TGFBI | transforming growth factor, beta-induced, 68 kD |
| 261. | SREBF1 | sterol regulatory element binding transcription factor 1 |
| 262. | MMP14 | matrix metalloproteinase 14 (membrane-inserted) |
| 263. | KCNQ1 | potassium voltage-gated channel, KQT-like subfamily, member 1 |
| 264. | TUBA1 | tubulin, alpha 1 (testis specific) |
| 265. | SELE | selectin E (endothelial adhesion molecule 1) |
| 266. | ATRX | alpha thalassemia/mental retardation syndrome X-linked (RAD54 homolog, *S. cerevisiae*) |
| 267. | IL2RG | interleukin 2 receptor, gamma (severe combined immunodeficiency) |
| 268. | IGFBP3 | insulin-like growth factor binding protein 3 |
| 269. | JAK3 | Janus kinase 3 (a protein tyrosine kinase, leukocyte) |
| 270. | CSF1R | colony stimulating factor 1 receptor, formerly McDonough feline sarcoma viral (v-fms) oncogene homolog |
| 271. | SHC1 | SHC (Src homology 2 domain containing) transforming protein 1 |
| 272. | CASP4 | caspase 4, apoptosis-related cysteine protease |
| 273. | PLA2G2A | phospholipase A2, group IIA (platelets, synovial fluid) |
| 274. | CXCR4 | chemokine (C—X—C motif), receptor 4 (fusin) |
| 275. | CDKN2B | cyclin-dependent kinase inhibitor 2B (p15, inhibits CDK4) |
| 276. | ARHA | ras homolog gene family, member A |
| 277. | SHH | sonic hedgehog homolog (*Drosophila*) |
| 278. | RARB | retinoic acid receptor, beta |
| 279. | MME | membrane metallo-endopeptidase (neutral endopeptidase, enkephalinase, CALLA, CD10) |
| 280. | CA2 | carbonic anhydrase II |
| 281. | PRKDC | protein kinase, DNA-activated, catalytic polypeptide |
| 282. | HIF1A | hypoxia-inducible factor 1, alpha subunit (basic helix-loop-helix transcription factor) |
| 283. | PRKCA | protein kinase C, alpha |
| 284. | CASP2 | caspase 2, apoptosis-related cysteine protease (neural precursor cell expressed, developmentally down-regulated 2) |
| 285. | DMBT1 | deleted in malignant brain tumors 1 |
| 286. | TGFB2 | transforming growth fator, beta 2 |
| 287. | TSC2 | tuberous sclerosis 2 |
| 288. | PSAP | prosaposin (variant Gaucher disease and variant metachromatic leukodystrophy) |
| 289. | XPC | xeroderma pigmentosum, complementation group C |
| 290. | THRA | thyroid hormone receptor, alpha (erythroblastic leukemia viral (v-erb-a) oncogene homolog, avian) |
| 291. | ERCC2 | excision repair cross-complementing rodent repair deficiency, complementation group 2 (xeroderma pigmentosum D) |
| 292. | MAPK1 | mitogen-activated protein kinase 1 |
| 293. | ATP6B1 | ATPase, H+ transporting, lysosomal (vacuolar proton pump), beta polypeptide, 56/58 kD, isoform 1 (Renal tubular acidosis with deafness) |

TABLE 1-continued

List of components which are disease-related and are detectable using the kit and/or method of the present invention.

| Number | Component | Comments |
|---|---|---|
| 294. | BAG1 | BCL2-associated athanogene |
| 295. | ACHE | acetylcholinesterase (YT blood group) |
| 296. | EGF | epidermal growth factor (beta-urogastrone) |
| 297. | DUSP1 | dual specificity phosphatase 1 |
| 298. | CASP6 | caspase 6, apoptosis-related cysteine protease |
| 299. | THRB | thyroid hormone receptor, beta (erythroblastic leukemia viral (v-erb-a) oncogene homolog 2, avian) |
| 300. | BAD | BCL2-antagonist of cell death |
| 301. | STAT6 | signal transducer and activator of transcription 6, interleukin-4 induced |
| 302. | ELN | elastin (supravalvular aortic stenosis, Williams-Beuren syndrome) |
| 303. | MAOA | monoamine oxidase A |
| 304. | F8 | coagulation factor VIII, procoagulant component (hemophilia A) |
| 305. | ENG | endoglin (Osler-Rendu-Weber syndrome 1) |
| 306. | HSPB1 | heat shock 27 kD protein 1 |
| 307. | HMGCR | 3-hydroxy-3-methylglutaryl-Coenzyme A reductase |
| 308. | PIM1 | pim-1 oncogene |
| 309. | PON1 | paraoxonase 1 |
| 310. | AHR | aryl hydrocarbon receptor |
| 311. | ITGB2 | integrin, beta 2 (antigen CD18 (p95), lymphocyte function-associated antigen 1; macrophage antigen 1 (mac-1) beta subunit) |
| 312. | PTGS1 | prostaglandin-endoperoxide synthase 1 (prostaglandin G/H synthase and cyclooxygenase) |
| 313. | PLCG1 | phospholipase C, gamma 1 (formerly subtype 148) |
| 314. | APOC3 | apolipoprotein C-III |
| 315. | NRG1 | neuregulin 1 |
| 316. | CD14 | CD14 antigen |
| 317. | IRF1 | interferon regulatory factor 1 |
| 318. | ALPL | alkaline phosphatase, liver/bone/kidney |
| 319. | ALDOA | aldolase A, fructose-bisphosphate |
| 320. | XPA | xeroderma pigmentosum, complementation group A |
| 321. | PDGFRA | platelet-derived growth factor receptor, alpha polypeptide |
| 322. | IL5 | interleukin 5 (colony-stimulating factor, eosinophil) |
| 323. | BMP2 | bone morphogenetic protein 2 |
| 324. | GSK3A | glycogen synthase kinase 3 alpha |
| 325. | STK11 | serine/threonine kinase 11 (Peutz-Jeghers syndrome) |
| 326. | GSK3B | glycogen synthase kinase 3 beta |
| 327. | CRYBB1 | crystallin, beta B1 |
| 328. | STAT5A | signal transducer and activator of transcription 5A |
| 329. | SCA1 | spinocerebellar ataxia 1 (olivopontocerebellar ataxia 1, autosomal dominant, ataxin 1) |
| 330. | RXRA | retinoid X receptor, alpha |
| 331. | NFKBIA | nuclear factor of kappa light polypeptide gene enhancer in B-cells inhibitor, alpha |
| 332. | MMP13 | matrix metalloproteinase 13 (collagenase 3) |
| 333. | TSHR | thyroid stimulating hormone receptor |
| 334. | MT2A | metallothionein 2A |
| 335. | TSSC3 | tumor suppressing subtransferable candidate 3 |
| 336. | RHO | rhodopsin (opsin 2, rod pigment) (retinitis pigmentosa 4, autosomal dominant) |
| 337. | GADD45A | growth arrest and DNA-damage-inducible, alpha |
| 338. | LCAT | lecithin-cholesterol acyltransferase |
| 339. | GSR | glutathione reductase |
| 340. | TOP2A | topoisomerase (DNA) II alpha (170 kD) |
| 341. | GPX1 | glutathione peroxidase 1 |
| 342. | FLT3 | fms-related tyrosine kinase 3 |
| 343. | CEBPB | CCAAT/enhancer binding protein (C/EBP), beta |
| 344. | TPM1 | tropomyosin 1 (alpha) |
| 345. | ABCA4 | ATP-binding cassette, sub-family A (ABC1), member 4 |
| 346. | KCNH2 | potassium voltage-gated channel, subfamily H (eag-related), member 2 |
| 347. | HNF4A | hepatocyte nuclear factor 4, alpha |
| 348. | DPYD | dihydropyrimidine dehydrogenase |
| 349. | MADH2 | MAD, mothers against decapentaplegic homolog 2 (*Drosophila*) |
| 350. | AFP | alpha-fetoprotein |
| 351. | TIMP2 | tissue inhibitor of metalloproteinase 2 |
| 352. | ITK | IL2-inducible T-cell kinase |
| 353. | ABL2 | v-abl Abelson murine leukemia viral oncogene homolog 2 (arg, Abelson-related gene) |
| 354. | SCYA4 | small inducible cytokine A4 |
| 355. | GCGR | glucagon receptor |

TABLE 1-continued

List of components which are disease-related and are detectable using the kit and/or method of the present invention.

| Number | Component | Comments |
|---|---|---|
| 356. | TCF3 | transcription factor 3 (E2A immunoglobulin enhancer binding factors E12/E47) |
| 357. | MYB | v-myb myeloblastosis viral oncogene homolog (avian) |
| 358. | LTA | lymphotoxin alpha (TNF superfamily, member 1) |
| 359. | LIF | leukemia inhibitory factor (cholinergic differentiation factor) |
| 360. | CYBB | cytochrome b-245, beta polypeptide (chronic granulomatous disease) |
| 361. | CTSL | cathepsin L |
| 362. | BCL2A1 | BCL2-related protein A1 |
| 363. | TFRC | transferrin receptor (p90, CD71) |
| 364. | RALGDS | ral guanine nucleotide dissociation stimulator |
| 365. | CYP2C8 | cytochrome P450, subfamily IIC (mephenytoin 4-hydroxylase), polypeptide 8 |
| 366. | CD38 | CD38 antigen (p45) |
| 367. | PRKCZ | protein kinase C, zeta |
| 368. | LAMR1 | laminin receptor 1 (67 kD, ribosomal protein SA) |
| 369. | IL12A | interleukin 12A (natural killer cell stimulatory factor 1, cytotoxic lymphocyte maturation factor 1, p35) |
| 370. | FGA | fibrinogen, A alpha polypeptide |
| 371. | EEF1A1 | eukaryotic translation elongation factor 1 alpha 1 |
| 372. | CYP21A2 | cytochrome P450, subfamily XXIA (steroid 21-hydroxylase, congenital adrenal hyperplasia), polypeptide 2 |
| 373. | CSF2 | colony stimulating factor 2 (granulocyte-macrophage) |
| 374. | TNFRSF5 | tumor necrosis factor receptor superfamily, member 5 |
| 375. | MBP | myelin basic protein |
| 376. | PTK2 | PTK2 protein tyrosine kinase 2 |
| 377. | KLK3 | kallikrein 3, (prostate specific antigen) |
| 378. | GALT | galactose-1-phosphate uridylyltransferase |
| 379. | APEX | APEX nuclease (multifunctional DNA repair enzyme) |
| 380. | EPHB2 | EphB2 |
| 381. | BIK | BCL2-interacting killer (apoptosis-inducing) |
| 382. | SLC2A1 | solute carrier family 2 (facilitated glucose transporter), member 1 |
| 383. | IL2RA | interleukin 2 receptor, alpha |
| 384. | IFNGR2 | interferon gamma receptor 2 (interferon gamma transducer 1) |
| 385. | AXL | AXL receptor tyrosine kinase |
| 386. | ADRB1 | adrenergic, beta-1-, receptor |
| 387. | RAD51 | RAD51 homolog (RecA homolog, E. coli) (S. cerevisiae) |
| 388. | GJA1 | gap junction protein, alpha 1, 43 kD (connexin 43) |
| 389. | EWSR1 | Ewing sarcoma breakpoint region 1 |
| 390. | CCR2 | chemokine (C—C motif) receptor 2 |
| 391. | RELA | v-rel reticuloendotheliosis viral oncogene homolog A, nuclear factor of kappa light polypeptide gene enhancer in B-cells 3, p65 (avian) |
| 392. | CTNNA1 | catenin (cadherin-associated protein), alpha 1 (102 kD) |
| 393. | MYO7A | myosin VIIA (Usher syndrome 1B (autosomal recessive, severe)) |
| 394. | F3 | coagulation factor III (thromboplastin, tissue factor) |
| 395. | EPHX1 | epoxide hydrolase 1, microsomal (xenobiotic) |
| 396. | CRK | v-crk sarcoma virus CT10 oncogene homolog (avian) |
| 397. | ENO1 | enolase 1, (alpha) |
| 398. | TGFBR1 | transforming growth factor, beta receptor I (activin A receptor type II-like kinase, 53 kD) |
| 399. | RAC1 | ras-related C3 botulinum toxin substrate 1 (rho family, small GTP binding protein Rac1) |
| 400. | ANPEP | alanyl (membrane) aminopeptidase (aminopeptidase N, aminopeptidase M, microsomal aminopeptidase, CD13, p150) |

A kit and/or method according to the invention may be used to detect infectious diseases. Some infectious diseases are life threatening and can appear in combination with other infections. Thus, the sooner they can be detected and characterised, the sooner an appropriate therapy can be established which is better for the patient. A kit and/or method as disclosed above can be used to detect said infectious agents. Components which may be detected according to the kit and/or method are those which form part of the infectious agent and/or are produced by the infectious agent. Viruses in diseased individuals detectable according to the kit and/or method include, but are not limited to HCV, HIV, HBV, HTLV, HPV (see also oncology). Bacteria in diseased individuals detectable according to the kit and/or method include, but are not limited to mycobacteria, syphilis, Staphylococcus aureus (screening of MRSA).

A kit and/or method according to the invention may be used to detect neurodegenerative diseases. Components which may be detected are those involved in degenerative diseases and include, but are not limited to beta-amyloids (Alzheimer's disease), hTAU, phosphoTAU and APOE.

A kit and/or method according to the invention may be used to detect prion-related diseases. Diseases associated with prions include Kreutzfeld Jacob disease and BSE.

A kit and/or method according to the invention may be used to detect diseases related to autoimmunity. Components which may be detected are those involved in autoimmunity include, but are not limited to ANA, Jo-1, Myeloperoxidase, RNP, Scl-70, Sm, SS-A.

A kit and/or method according to the invention may be used to detect diseases related to allergy. Components which may be detected are those involved in allergy and include, but are not limited to IgE, IgG-subclasses and circulating antibodies.

A kit and/or method according to the invention may be used in the field of genomics to detect susceptibility to disease, possibility of passing conditions to offspring, single nucleotide polymorphisms etc. Examples of fields in which a kit and/or method of the invention apply include, but are not limited to HLA typing, p53 polymorphism (SNP) related to the sensitivity of developing a cervix carcinoma after an HPV 16 infection, hypertension, detection of polymorphism in relation to the susceptibility for osteoporosis, detection of mutations in Factor V (Leiden), detection of the genetic susceptibility for SIDS (cot death), hereditary: paternity tests, etc., detection of micro satellite instability, detection of the success rate of therapy related to cessation of smoking, detection of disturbances in the metabolism of lipids including cholesterol (HDL, LDL, VLDL and their receptors) in relationship to cardiovascular diseases such as atheromathosis, detection of genomic defects related to obesitas, detection of genomic defects related to diabetes, detection of mutations associated with drug resistance (to HIV, etc.), screening and detection of systic fibrosis (CFTR mutations), detection of mutations in the mitochondrial genome related to a number of diseases as: neurogenic muscular weakness, retinitis pigmentosa, ocular myopathy, etc.

A kit and/or method according to the invention may be used in the fields related to environmental testing. Many applications are related to water where it is important to have a technology which is sensitive enough to detect very small amounts of contaminants or unwanted compounds in reasonably economical manner. Examples of environmental tests include:

- checking (monitoring) of yeast infections in swimming pool water
- monitoring of biological pollution in general
- biological contaminants in potable water (amoebae, coliform bacteria, etc.).

In addition to water testing, the environmental testing for genetically modified organisms may be performed according to a kit and/or method of the present invention. Genetically Modified Organisms can be detected, or samples screened for the absence of. Checking for possible modifications is sometimes difficult, however, a sensitive technique such as that provided by the present method is suitable for such a purpose.

A kit and/or method according to the invention may be used to detect the infection of food.

Inspection of all places and objects related to food needs sensitive methods, and kit and/or method of the present invention provide the required sensitivity. Furthermore, a kit and/or method of the present invention can be performed and the results obtained at the site at which the inspection takes place, so obviating the need to send samples to a lab. Thus, steps can be taken immediately if necessary. Examples of the agents that may be detected include *Listeria, Salmonella*, prions (for BSE). Molecules which may be detected assay are those which form part of the agent and/or are produced by the agent.

A kit and/or method of the present invention may be applied in standard biochemical detection protocols. All the existing types of blotting techniques show an enhancement in sensitivity using the method disclosed herein, without the requirement for radioisotopes or chemilluminescent detection such as photographic plates, or phosphor screens. It is also possible to use the method in combination with image analysis. Examples of blotting protocols that may use methods of the present invention include but are not limited to Western blotting, Northern blotting, Southern blotting, vacuum blotting, contact blotting, reversed line blot and related techniques, dot blotting, micro-arrays, macro-arrays.

Another embodiment of the present invention is a use of a method or kit as described herein for the quantitative and/or qualitative detection of components in a sample. Another embodiment of the present invention is a use of a method or kit as described herein for imaging components in a system by magnetic resonance.

Staining of Microscopy Slides

Another embodiment of the present invention is a method for staining sections of cells and/or tissues suitable for visualisation using microscopy. Types of microscopy may be any, and include, but are not limited to light microscopy, tunneling electron microscopy, scanning electron microscopy, transmission electron microscopy.

According to one aspect of the invention, a method for staining components in cell and/or tissue sections, said staining suitable for visualisation using microscopy comprises the following steps:

A) incubating section with one or more biotinylated probes directed against a component,
B) incubating section with streptavidin-metal particle complex,
C) incubating section with conjugate comprising:
   one or more biotins,
   one or more polymers, and
   metal particles bound to said polymer, and
D) optionally incubating the section with metal enhancement reagent.

Biotinylated probes, strepavidin-metal particle complex, conjugate and the kinds of metal particles are already described above. The introduction of other steps into the method, such as wash steps, for example, may be known by the skilled artisan practicing in the field of immunohistochemistry. Preferably, a wash is performed after every step. Examples of wash buffers are described above. The "metal enhancement reagent" of step D) is also described above.

Another embodiment of the present invention is a kit for staining sections of cells and/or tissues suitable for visualisation using microscopy comprising one or more of the following:

streptavidin-metal particle complex
conjugate
biotinylated probe
metal enhancement reagent
reagents for biotinylation A kit for staining sections according to the present invention allows a skilled artisan to perform one or more steps of the method disclosed herein, in a convenient manner. The kit may allow a method of the present invention to be performed without the need to measure or determine the concentrations of reagents, so enabling a fast and reproducible staining of sections.

In another aspect of the invention, the kit for staining sections enables the skilled person to perform one or more of the methods disclosed herein. The kit may comprise one or more additional containers in which reagents are present enabling the skilled person to perform the complete method. Alternatively, the kit may comprise a minimum number of containers, such as only streptavidin-metal particle complex, for example, that enables a skilled person to perform the method disclosed herein.

In another aspect of the invention, the kit contains instructions for use. In another aspect of the invention the instructions describe a method of the invention as disclosed herein.

A method and/or kit of the present invention for staining sections of cells may equally well be performed on any cell or tissue in the applications of flow cytometry and in situ hybridisation, wherein the visualisation of cells and tissues is necessary. Due to the sensitivity of the method as disclosed herein, target antigens (proteins and other substances) can be visualised in tissues and cells with antibodies and, using in situ hybridization, they can be visualised by use of nucleic acid probes.

EXAMPLES

Section 1

Materials and Methods

Oligonucleotides

```
                                      (SEQ ID NO: 1)
Target:       5' GGATTATTGTTAAATATTGATAAGGAT 3'

(SEQ ID NO: 2)
Visualisation 5' ATCCTTATCAATATT 3'
oligo:

(SEQ ID NO: 3)
Oligo op drager: 5' TAACAATAATCC 3'
```

The above mentioned oligonucleotides are derived from the Anthrax lethal factor genome.

Nylon or Nitrocellulose Coated Slides

Coated slides such as Nytran coated slides, nitrocellulose coated slides were purchased from Schleicher and Schuell and printed with DNA capturing oligonucleotides using a MICROCAST micro-arrayer.

Modified DNA oligonucleotides were custom made by Eurogentec (Belgium) and in varying concentrations dissolved in printing buffer (6×SSC).

Micro-arrays were manufactured by printing varying oligonucleotide concentrations ranging from 0.001 μM to 20 μM on the coated glass slide. Negative controls consisted of printing buffer without DNA oligonucleotides and printing buffer with a DNA oligonucleotide complementary to a non-relted sequence in the same concentration as the capturing oligonucleotide of interest. After drying during 30 minutes at room temperature, the slides were baked at 80° C. for 30 minutes. The DNA printed Nytran coated slides were cross linked using UV radiation according to previously described protocols. Slides were stored dust-free at 4° C. until further analysis.

Silane Coated Slides

Silane coated slides were purchased from Schleicher and Schuell and printed with DNA oligonucleotides using a MICROCAST micro-arrayer.

DNA oligonucleotides were custom made by Eurogentec (Belgium) and in varying concentrations dissolved in printing buffer. Silane coated slides and modified oligonucleotides were activated according to previously described protocols.

Micro-arrays were manufactured by printing varying oligonucleotide concentrations ranging from 0.001 μM to 20 μM on the activated silane coated glass slide. After drying for 30 minutes at room temperature, the printed slides were stored dust-free at 4° C.

Classical Glass Slides

Classical microscopical glass slides were washed with twice distilled water followed by immersion in a 10% NaOH solution at room temperature, and followed by an ultrasound treatment for 30 minutes. After several washes in running tap water, slides were washed several times with twice distilled water. Afterwards the slides were dried at 80° C.

Modified oligonucleotides were acivated and coupled with aminosilane according to previously described protocols (Kumar et al. Silanized nucleic acids: a general platform for DNA immobilization. Nucleic acids res 2000; 28: p71.).

The silanized oligonucleotides were dissolved in printing buffer (50% DMSO,) and printed as described above.

Printing of the Micro-Arrays

Micro-arrays were printed with each concentration of capturing oligonucleotides and the above described appropriate negative controls, a total of six times.

Section 2

Experiments to Compare Methods of Detection Using Gold and Enzyme Visualisations in Combination with Polymer Amplification and Other Technologies Part 1—Visualization Experiments of Labeled Oligonucleotides in the Above Described Solid Assays Experiment 1—Part 1: Visualization of Labeled Oligonucleotides Using Streptavidin Micro-arrays were printed as described previously. All concentrations ranging from 0.001 μM to 20 μM were spotted six times using biotinylated probes. Micro-arrays were baked at 80° C. for 30 minutes and stored dust-free at 4° C. until use.

Slides were washed twice with PBS (pH 7.4) supplemented with 3% protein.

Slides were incubated with the same PBS/protein buffer solution for 30 minutes at room temperature.

Slides were incubated with streptavidin/alkaline phosphatase (concentration 1/1000 in PBS/protein buffer) (Roche Germany) for 60 minutes followed by three washes with PBS/protein buffer at room temperature.

The alkaline phosphatase reaction was developed by incubating the slides with napthol substrate in appropriate buffer (Dako, Denmark) for 30 minutes at room temperature.

Experiment 2—Part 1: Visualization of Labeled Oligonucleotides Using Streptavin Labeled with Gold Particles Micro-arrays were printed as described previously. All concentrations ranging from 0.001 μM to 20 μM were spotted six times. Micro-arrays were baked at 80° C. for 30 minutes and stored dust-free at 4° C. until use.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein for 5 minutes.

Slides were incubated with streptavidin/gold 0.8 nm (concentration 1/50 in washing buffer) or 6 nm (concentration 1/20 in washing buffer) (Sigma, U.S.A.) for 120 minutes followed by six washes with washing buffer at room temperature.

Slides were rinsed three times for five minutes with PBS, followed by distilled water.

The gold particles were visualized by metal enhancement (Sigma U.S.A.) for 15 minutes.

Experiment 3—Part 1: Visualization of Labeled Oligonucleotides Using Monoclonal Antibodies Labeled with Gold Particles Micro-arrays were printed as described previously. All concentrations ranging from 0.001 µM to 20 µM were spotted in six times. Micro-arrays were baked at 80° C. for 30 minutes and stored dust-free at 4° C. until use.

Slides were washed twice with PBS (pH 7.4) supplemented with 3% protein.

Slides were incubated with the same PBS/protein buffer solution during 30 minutes at room temperature.

Slides were washed twice with special washing buffer (PBS pH 7.4 supplemented—with 0.2% protein) for 5 minutes.

Slides were incubated with monoclonal antibody/gold 0.8 nm (concentration 1/50 in washing buffer), 6 nm (concentration 1/20 in washing buffer) or 30 nm for 120 minutes followed by six washes with washing buffer at room temperature.

Slides were rinsed three times for five minutes with PBS, followed by distilled water.

The gold particles were visualized by metal enhancement during 15 minutes.

Experiment 4—Part 1: Visualization of Labeled Oligonucleotides Using Polyclonal Antibodies Labeled with Gold Particles Micro-arrays were printed as described previously. All concentrations ranging from 0.001 µM to 20 µM were spotted six times. Micro-arrays were baked at 80° C. for 30 minutes and stored dust-free at 4° C. until use.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes.

Slides were incubated with monoclonal antibody/gold 0.8 nm (concentration 1/50 in washing buffer) or 6 nm (concentration 1/20 in washing buffer) for 120 minutes followed by six washes with washing buffer at room temperature.

Slides were rinsed three times for five minutes with PBS, followed by distilled water.

The gold particles were visualized by metal enhancement during 15 minutes.

Experiment 5—Part 1: Visualization of Labeled Oligonucleotides Using Streptavidin-Gold, Biotinylated Monoclonal and Polyclonal Antibodies Followed by Streptavidin Labeled with Gold Micro-arrays were printed as described previously. All concentrations ranging from 0.001 µM to 20 µM were spotted six times. Micro-arrays were baked at 80° C. for 30 minutes and stored dust-free at 4° C. until use.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes and incubated with the same washing buffer.

Slides were incubated with streptavidin labeled with gold particles ranging from 0.8 nm to 40 nm during 30 minutes followed by six washes with washing buffer at room temperature.

Slides were incubated with biotinylated monoclonal or biotinylated polyclonal antibody labeled with gold particles ranging from 0.8 nm to 40 nm for 30 minutes followed by six washes with washing buffer at room temperature.

Slides were incubated with streptavidin labeled with gold particles ranging from 0.8 nm to 40 nm during 30 minutes followed by six washes with washing buffer at room temperature Experiment 6—Part 1: Visualization of Labeled Oligonucleotides Using Gold Labeled Streptavidin Followed by Biotinylated Albumin and Gold Particles Micro-arrays were printed as described previously. All concentrations ranging from 0.001 µM to 20 µM were spotted six times. Micro-arrays were baked at 80° C. for 30 minutes and stored dust-free at 4° C. until use.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) during 5 minutes and incubated with the same washing buffer.

Slides were incubated with streptavidin labeled with gold particles ranging from 0.8 nm to 40 nm for 30 minutes followed by six washes with washing buffer at room temperature.

Slides were incubated with albumin coated with numerous biotin molecules and labeled with gold particles ranging from 0.8 nm to 40 nm for 30 minutes followed by six washes with washing buffer followed by distilled water.

The gold particles were visualized by metal enhancement for 15 minutes.

Experiment 7—Part 1: Visualization of Labeled Oligonucleotides Using 200 nm Supermagnetic Particles Coated with Streptavidin Followed by Biotinylated Albumin and Gold Particles Micro-arrays were printed as described previously. All concentrations ranging from 0.001 µM to 20 µM were spotted six times. Micro-arrays were baked at 80° C. for 30 minutes and stored dust-free at 4° C. until use.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2 protein) for 5 minutes and incubated with the same washing buffer.

Slides were incubated with 200 nm nanoparticles coated with streptavidin followed by six washes with washing buffer at room temperature.

Slides were incubated with albumin coated with numerous biotin molecules and labeled with gold particles ranging from 0.8 nm to 40 nm for 30 minutes followed by six washes with washing buffer followed by distilled water.

The gold particles were visualized by metal enhancement for 15 minutes.

Experiment 8—Part 1: Visualization of Labeled Oligonucleotides Using 200 nm Particles Coated with Streptavidin, Followed by Polymer and Gold Particles.

Micro-arrays were printed as described previously. All concentrations ranging from 0.001 µM to 20 µM were spotted six times. Micro-arrays were baked at 80° C. for 30 minutes and stored dust-free at 4° C. until use.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes and incubated with the same washing buffer.

Slides were incubated with 200 nm nanoparticles coated with streptavidin followed by six washes with washing buffer at room temperature.

Slides were incubated with dextran polymer or poly-L-lysin polymer coated with numerous biotin molecules and labeled with gold particles ranging from 0.8 nm to 40 nm for 30 minutes followed by six washes with washing buffer followed by distilled water.

The gold particles were visualized by metal enhancement during 15 minutes.

Part 2: Hybridization Experiments of Labeled Oligonucleotides Attached at the Above Described Solid Assays Experiment 2.1—Part 2: Visualization of Labeled Oligonucleotides Using Streptavidin Micro-arrays were printed as described previously. All concentrations ranging from 0.001 µM to 20 µM were spotted six times including adequate positive and negative controls. Micro-arrays were baked at 80° C. for 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA consisting of labeled oligonucleotide ay a concentration of 250 ng/ml hybridization mixture. Hybridization was carried out overnight at 37° C.

Slides were washed twice with 2×SSC at room temperature.

Slides were washed twice with PBS (pH 7.4) supplemented with 3% protein.

Slides were incubated with the same PBS/protein buffer solution for 30 minutes at room temperature.

Slides were incubated with streptavidin/alkaline phosphatase (concentration 1/1000 in PBS/protein buffer) for 60 minutes followed by three washes with PBS/protein buffer at room temperature.

The alkaline phosphatase reaction was developed by incubating the slides with napthol substrate in appropriate buffer for 30 minutes at room temperature.

Experiment 2.2—Part 2: Visualization of Labeled Oligonucleotides Using Streptavin Labeled with Gold Particles Micro-arrays were printed as described previously. All concentrations ranging from 0.001 µM to 20 µM were spotted six times. Micro-arrays were baked at 80° C. for 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA consisting of labeled oligonucleotide in a concentration of 250 ng/ml hybridization mixture. Hybridization was carried out overnight at 37° C.

Slides were washed twice with 2×SSC at room temperature.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) during 5 minutes.

Slides were incubated with streptavidin/gold 0.8 nm (concentration 1/50 in washing buffer) or 6 nm (concentration 1/20 in washing buffer) for 120 minutes followed by six washes with washing buffer at room temperature.

Slides were rinsed three times during five minutes with PBS, followed by distilled water.

The gold particles were visualized by metal enhancement for 15 minutes.

Experiment 3—Part 2: Visualization of Labeled Oligonucleotides Using Monoclonal Antibodies Labeled with Gold Particles Micro-arrays were printed as described previously. All concentrations ranging from 0.001 µM to 20 µM were spotted in six times. Micro-arrays were baked at 80° C. for 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA consisting of labeled oligonucleotide at a concentration of 250 ng/ml hybridization mixture. Hybridization was carried out overnight at 37° C.

Slides were washed twice with 2×SSC at room temperature.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes.

Slides were incubated with monoclonal antibody/gold 0.8 nm (concentration 1/50 in washing buffer) or 6 nm (concentration 1/20 in washing buffer), or 30 nm for 120 minutes followed by six washes with washing buffer at room temperature.

Slides were rinsed three times for five minutes with PBS, followed by distilled water.

The gold particles were visualized by metal enhancement for 15 minutes.

Experiment 4—Part 2: Visualization of Labeled Oligonucleotides Using Polyclonal Antibodies Labeled with Gold Particles Micro-arrays were printed as described previously. All concentrations ranging from 0.001 µM to 20 µM were spotted six times. Micro-arrays were baked at 80° C. for 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA consisting of labeled oligonucleotide in a concentration of 250 ng/ml hybridization mixture. Hybridization was carried out overnight at 37° C.

Slides were washed twice with 2×SSC at room temperature.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes.

Slides were incubated with monoclonal antibody/gold 0.8 nm (concentration 1/50 in washing buffer) or 6 nm (concentration 1/20 in washing buffer) for 120 minutes followed by six washes with washing buffer at room temperature.

Slides were rinsed three times for five minutes with PBS, followed by distilled water.

The gold particles were visualized by metal enhancement for 15 minutes.

Experiment 5—Part 2: Visualization of Labeled Oligonucleotides Using Streptavidin-Gold, Biotinylated Monoclonal and Polyclonal Antibodies Followed by Streptavidin Labeled with Gold Micro-arrays were printed as described previously. All concentrations ranging from 0.001 µM to 20 µM were spotted six times. Micro-arrays were baked at 80° C. for 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA consisting of labeled oligonucleotide in a concentration of 250 ng/ml hybridization mixture. Hybridization was carried out overnight at 37° C.

Slides were washed twice with 2×SSC at room temperature

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes and incubated with the same washing buffer.

Slides were incubated with streptavidin labeled with gold particles ranging from 0.8 nm to 40 nm for 30 minutes followed by six washes with washing buffer at room temperature Slides were incubated with biotinylated monoclonal or biotinylated polyclonal antibody labeled with gold particles ranging from 0.8 nm to 40 nm for 30 minutes followed by six washes with washing buffer at room temperature.

Slides were incubated with streptavidin labeled with gold particles ranging from 0.8 nm to 40 nm for 30 minutes followed by six washes with washing buffer at room temperature.

Experiment 6—Part 2: Visualization of Labeled Oligonucleotides Using Gold Labeled Streptavidin Followed by Biotinylated Albumin and Gold Particles The slides were prehybridized with hybridization mixture supplemented with sonicated herring sperm DNA (150 µg/5 ml hybridization mixture) for 2 hours at room temperature.

Hybridization assay was set up using target DNA consisting of labeled oligonucleotide in a concentration of 250 ng/ml hybridization mixture. Hybridization was carried out overnight at 37° C.

Slides were washed twice with 2×SSC at room temperature

Micro-arrays were printed as described previously. All concentrations ranging from 0.001 µM to 20 µM were spotted six times. Micro-arrays were baked at 80° C. for 30 minutes and stored dust-free at 4° C. until use.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes and incubated with the same washing buffer.

Slides were incubated with streptavidin labeled with gold particles ranging from 0.8 nm to 40 nm for 30 minutes followed by six washes with washing buffer at room temperature.

Slides were incubated with albumin coated with numerous biotin molecules and labeled with gold particles ranging from 0.8 nm to 40 nm for 30 minutes followed by six washes with washing buffer followed by distilled water.

The gold particles were visualized by metal enhancement for 15 minutes.

Experiment 7—Part 2: Visualization of Labeled Oligonucleotides Using 200 nm Supermagnetic Particles Coated with Streptavidin Followed by Biotinylated Albumin and Gold Particles Micro-arrays were printed as described previously. All concentrations ranging from 0.001 µM to 20 µM were spotted six times. Micro-arrays were baked at 80° C. for 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA consisting of labeled oligonucleotide in a concentration of 250 ng/ml hybridization mixture. Hybridization was carried out overnight at 37° C.

Slides were washed twice with 2×SSC at room temperature

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes and incubated with the same washing buffer.

Slides were incubated with 200 nm nanoparticles coated with streptavidin followed by six washes with washing buffer at room temperature.

Slides were incubated with albumin coated with numerous biotin molecules and labeled with gold particles ranging from 0.8 nm to 40 nm for 30 minutes followed by six washes with washing buffer followed by distilled water.

The gold particles were visualized by metal enhancement for 15 minutes.

Experiment 8—Part 2: Visualization of Labeled Oligonucleotides Using 200 nm Particles Coated with Streptavidin, Followed by Polymer and Gold Particles.

Micro-arrays were printed as described previously. All concentrations ranging from 0.001 µM to 20 µM were spotted six times. Micro-arrays were baked at 80° C. for 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA consisting of labeled oligonucleotide in a concentration of 250 ng/ml hybridization mixture. Hybridization was carried out overnight at 37° C.

Slides were washed twice with 2×SSC at room temperature

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes and incubated with the same washing buffer.

Slides were incubated with 200 nm nanoparticles coated with streptavidin followed by six washes with washing buffer at room temperature.

Slides were incubated with dextran polymer or poly-L-lysin polymer coated with numerous biotin molecules and labeled with gold particles ranging from 0.8 nm to 40 nm for 30 minutes followed by six washes with washing buffer followed by distilled water.

The gold particles were visualized by metal enhancement for 15 minutes.

Results and Discussion

Results of experiments without signal amplification:

Experiment 1—Visualization with Streptavidin-Enzyme

Hybridization was visualized as deep red or dark brown spots according to the used enzyme and substrate. The spots were easy discernible at the white background of the slide. Background staining was not present. Visualization was achieved with spotted molecular probe concentration ranging from 0.2 mM to 0.02 mM.

Experiment 2—Visualization with Streptavidin Gold 0.8 nm and 6 nm

Hybridization was visualized as deep black grey spots according to the used metal enhancement. The spots were easy discernible at the white background of the slide. Background staining was not presented. Visualization was achieved with spotted molecular probe concentration ranging from 0.2 mM to 0.02 mM.

Experiment 3—Visualization with Monoclonal Mouse Antibodies with Gold 0.8 nm and 6 nm Hybridization was visualized as deep black spots according to the used metal enhancement.strate. The spots were easy discernible at the white background of the slide. Background staining was not presented. Visualization was achieved with spotted molecular probe concentration ranging from 0.2 mM to 0.002 mM. However the signal was stronger with the 6 nm gold compared to the 0.8 nm gold and sharper than with the streptavidin-gold method. In comparison with the polyclonal antibodies the signal was slightly sharper.

Experiment 3—Visualization with Monoclonal Mouse Antibodies with Gold 30 nm

Hybridization was faintly visualized as light rosa spots only at the highest spot concentration of 0.2 mM. Metal enhancement did not yield significant signal strenghtening. Background staining was considerable.

Experiment 4—Visualization with Polyclonal Goat Antibodies with Gold 0.8 nm and 6 nm Hybridization was visualized as deep black spots according to the used metal enhancement.strate. The spots were easy discernible at the white background of the slide. Background staining was not presented. Visualization was achieved with spotted molecular probe concentration ranging from 0.2 mM to 0.002 mM. However the signal was stronger with the 6 nm gold compared to the 0.8 nm gold and sharper than with the streptavidin-gold method.

Results of Experiments with Signal Amplification:

Experiment 5—Visualization with Streptavidin/Gold-Biotinylated Monoclonal and Polyclonal Antibodies Followed by Streptavidin Labeled with Gold.

Hybridization was visualized as deep black spots. The spots were easy discernible at the white background of the slide. Background staining was slight. Visualization was achieved with spotted molecular probe concentration ranging from 0.1 mM to 0.0001 mM.

Experiment 6—Visualization with Gold Labeled Streptavidin (Gold 0.8 nm, 6 nm and 30 nm) Followed by Biotinylated Albumin and Gold Partikels 0.8, 6 nm and 30 nm Hybridization was visualized as deep black spots according to the used metal enhancement.strate. The spots were easy discernible at the white background of the slide. Background staining was very slight. Visualization was achieved with spotted molecular probe concentration ranging from 0.1 mM to 0.0001 mM. However the signal was stronger with the 0.8 nm gold compared to the 6 nm gold and sharper than with the streptavidin-enzym method. The 30 nm gold particles gave a slight rosa reaction barely discernible with the naked eye.

Experiment 7—Visualization with Superparamagnetic Particle 200 Nm-Streptavidin/Gold-Albumin/Gold/Biotin Hybridization was visualized as deep grey to black brown spots. The spots were easy discernible at the white background of the slide. Background staining was low to moderately. Visualization was achieved with spotted molecular probe concentration ranging from 0.2-mM to 0.0002 mM.

Experiment 8—Visualization with Streptavidin Gold 0.8 Nm and 6 Nm-Polymer/Gold

Hybridization was visualized as deep black grey spots according to the used metal enhancement. The spots were easy discernible at the white background of the slide. Background staining was absent. Visualization was achieved with spotted molecular probe concentration ranging from 0.2 mM to 0.0002 mM. However the signal was stronger with the 6 nm gold compared to the 0.8 nm gold and sharper than with the streptavidin-gold method.

Section 3

Detection and Subtyping of HPV DNA

Micro-arrays were printed as described previously using specific oligonucleotides detecting HPV 16, HPV18, HPV 31, HPV 33, HPV 35, HPV 52 and HPV 58. The oligonucleotides were dissolved in printing buffer resulting in an end concentration of 10 μM and were spotted six times including adequate positive and negative controls using a Microcast manual arrayer.

This results in a micro-array with 7 seven rows, each row consisting of six identical spots, representing the seven above described HPV types. The negative controls consisted of printing buffer without DNA and a second negative control consisted of an oligonucleotide coding for a non-related gene segment and were printed as two rows consisting of six spots where one row consisted out of printing buffer without DNA and another row consisted of non-related DNA oligonucleotide.

The positive control consisted of an equimolar mixture of the above described HPV type specific oligonucleotides printed in one row consisting of six identical spots.

After printing the micro-arrays were air dried at room temperature for 15 minutes.

Micro-arrays were baked at 80° C. for 30 minutes and stored dust-free at 4° C. until use.

The slides were prehybridized with hybrimix hybridization buffer (Sigma, USA) supplemented with sonicated herring sperm DNA (150 μg/5 ml hybridization mixture) (Sigma, USA) for 2 hours at room temperature.

Hybridization with PCR Labeled Amplification Product

Hybridization assay was set up using PCR amplified HPV DNA.

During the PCR reaction the amplification product was labeled using a biotin labeled primer.

In another experiment the PCR was set up with two unlabeled primers.

Ten microliter of the PCR amplification product was denatured with 10 μl denaturation solution (NAOH/EDTA). The denatured DNA solution was added to 2 ml of hybridization mixture. The micro-arrays were covered with a cover slip and hybridized overnight at 37° C. in a humid chamber.

Slides were washed twice with 2×SSC supplemented with 0.1% SDS at room temperature.

Slides were washed twice with PBS (pH 7.4) supplemented with 3% protein.

The hybridization of the biotin labeled PCR product was revealed using one of the methods described above.

Visualisation with Streptavidin-Alkaline Phosphatase

Slides were incubated with the same PBS/protein buffer solution for 30 minutes at room temperature.

Slides were incubated with streptavidin/alkaline phosphatase (concentration 1/1000 in PBS/protein buffer) for 60 minutes followed by three washes with PBS/protein buffer at room temperature.

The alkaline phosphatase reaction was developed by incubating the slides with napthol substrate in appropriate buffer for 30 minutes at room temperature.

Visualisation with Streptavidin-Gold

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes.

Slides were incubated with streptavidin/gold 0.8 nm (concentration 1/50 in washing buffer) or 6 nm (concentration 1/20 in washing buffer) for 120 minutes followed by six washes with washing buffer at room temperature.

Slides were rinsed three times for five minutes with PBS.

The gold particles were visualized by metal enhancement for 15 minutes.

Visualisation with Mono- or Polyclonal Anti-Biotin Antibody

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes.

Slides were incubated with monoclonal or polyclonal antibody/gold 0.8 nm (concentration 1/50 in washing buffer) or 6 nm (concentration 1/20 in washing buffer) for 120 minutes followed by six washes with washing buffer at room temperature.

Slides were rinsed three times for five minutes with PBS.

The gold particles were visualized by metal enhancement for 15 minutes.

Visualisation Using Streptavidin-Gold Followed by Signal Amplification with Biotinylated Polymer Technology Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes and incubated with the same washing buffer.

Slides were incubated with streptavidin labeled with gold particles ranging from 0.8 nm to 40 nm for 30 minutes followed by six washes with washing buffer at room temperature.

Slides were incubated with dextran polymer or poly-L-lysine polymer coated with numerous biotin molecules for 30 minutes followed by six washes with washing buffer.

Slides were incubated with monoclonal or polyclonal anti-biotin antibody or streptavidin labeled with gold particles ranging from 0.8 nm to 40 nm for 60 minutes followed by six washes with washing buffer at room temperature Slides were rinsed three times for five minutes with PBS.

The gold particles were visualized by metal enhancement for 15 minutes.

Hybridization with Unlabeled PCR Amplification Product, Visualization Using an Intercalating Agent, Signal Amplification with Polymer Technology and Gold.

Hybridization assay was set up using PCR amplified HPV DNA.

In this part of the experiment the PCR was set up with two unlabeled primers.

Ten microliter of the PCR amplification product was denatured with 10 μl denaturation solution (NAOH/EDTA). The denatured DNA solution was added to 2 ml of hybridization mixture. The micro-arrys were covered with a cover slip and hybridized overnight at 37° C. in a humid chamber.

Slides were washed twice with 2×SSC supplemented with 0.1% SDS at room temperature.

Slides were washed twice with PBS (pH 7.4) supplemented with 3% protein.

The hybridization of the unlabeled PCR product with its capture oligonucleotide at the micro-array was revealed using an intercalating agent, type DAPI (4',6-Diamidino-2-phenylindole dihydrochloride) that was coupled with streptavidin.

Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes and incubated with the same washing buffer.

Slides were incubated with dapi or doxorubicine conjugated with streptavidin labelled with gold particles ranging from 0.8 nm to 40 nm for 60 minutes followed by six washes with washing buffer at room temperature.

Slides were incubated with biotinylated albumin/gold or poly-L-lysine polymer coated with biotin molecules for 30 minutes followed by six washes with washing buffer.

Slides were incubated with streptavidin labeled with gold particles ranging from 0.8 nm to 40 nm for 60 minutes followed by six washes with washing buffer at room temperature Slides were rinsed three times for five minutes with PBS.

The gold particles were visualized by metal enhancement for 15 minutes.

Results and Discussion

Hybridized micro-arrays showed areas with very sharp black or red coloured spots in some areas depending on the used substrate. Other areas did not show any signal. Background signal was completely absent.

Hybridization was revealed as easy discernible bright spots coloured deep red when using the alkaline phophatase technique for visualization or as deep grey to black spots when using gold-metal enhancement technology. The results were easily evaluated with the naked eye. The best results were obtained with gold labeled antibodies used in a polymer amplification technique and streptavidin-gold-albumin method.

Negative controls did not show any sign of positivity. The positive control was strongly positive. In one experiment the presence of HPV 16 was revealed and in another experiment the presence of HPV 18 was highlighted. Cross-hybridization with other molecular probes was not noted. Samples without HPV DNA did not give a signal at the micro-array.

Section 4

Application of Immunohistochemistry: Visualization of In Situ of Monoclonal Antibodies Using Gold Labeled Monoclonal and Polyclonal Antibodies in a Polymer Enhanced Amplification Technique Sections of 5 μm were cut from paraffin embedded formalin fixed tissue of squamous lung carcinoma and adhered to poly-1-lysine coated glass slides, dried at 55° C. overnight and stored dust-free at room temperature. The sections were deparaffinized in two rinses of xylene substitute, followed by rehydratation in an descending series of alcohols down to deionized water. Slides were washed twice with PBS (pH 7.4)

and incubated with anti-ema (epithelial membrane antigen) monoclonal mouse antibody (Dakopatts Denmark) according to the instructions of the manufacturer). Slides were washed twice with PBS (pH 7.4) supplemented with 3% protein.

Slides were incubated with the same PBS/protein buffer solution for 30 minutes at room temperature.

Slides were washed twice with special washing buffer (PBS pH 7.4 supplemented with 0.2% protein) for 5 minutes and incubated with the same washing buffer.

Slides were incubated with biotinylated monoclonal or polyclonal anti-mouse antibody labelled with gold particles ranging from 0.8 nm to 40 nm for 60 minutes followed by six washes with washing buffer at room temperature.

Slides were incubated with streptavidin polymer (dextran or poly-L-lysine) coated with gold particles for 30 minutes followed by six washes with washing buffer.

Optionally slides were incubated with biotinylated albumin labelled with gold particles ranging from 0.8 nm to 40 nm for 30 minutes followed by six washes with washing buffer at room temperature Slides were rinsed three times for five minutes with PBS, followed by distilled water.

The gold particles were visualized by metal enhancement for 15 minutes.

The results showed clear and sharp staining with excellent contrast.

(a) applying one or more samples onto a solid support,
(b) contacting the solid support after step a) with one or more biotin-labeled probes,
(c) contacting the solid support after step b) with a complex of streptavidin and/or avidin and non-covalently bound-metal particle,
(d) contacting the solid support after step c) with a conjugate comprising:
one or more biotins,
one or more polymers, and
metal particles bound to said polymer,
forming an association between the sample bound to the solid support of step a), the biotin-labeled probe of step b) the metal particle complex of step c), and the conjugate of step d), wherein the complex of step c) and conjugate of step d) amplify interaction between the probe and the component to be detected,
(e) optionally contacting the solid support with a metal enhancement reagent, and
(f) reading the solid support after step d) or e) to quantitatively and/or qualitatively detect said component.

2. The method according to claim 1 wherein the reading of step (f) further comprises the use of a colour chart.

3. The method according to claim 1 wherein the polymer of a conjugate is a biologically inert polymer, capable of binding to one or more metal particles.

What is claimed is:

1. Method for quantitatively and/or qualitatively detecting one or more components in a sample, each component capable of binding to a probe, comprising steps in the following order:

4. The method according to claim 1, wherein a polymer is any of albumin or dextran.

5. The method according to claim 1 wherein the conjugate comprises one or more particles of gold, silver, iron, nickel, gadolinium, lead, uranium, caesium, platinum, rhodium, technetium, tellurium, selenium, silicon, silicium, cupper, tin, rhenium, europium, aluminium, germanium, chromium, cadmium, niobium, titanium, magnesium, manganese, molybdenum, antimony, americium, lithium, and/or wolfram.

6. The method according to claim 1 wherein the conjugate comprises one or more gold particles.

7. The method according to claim 1 wherein the metal particles of the conjugate have a diameter between 0.6 to 40 nm.

8. The method according to claim 1 wherein said probe is an antibody, nucleic acid, peptide nucleic acid, polypeptide or peptide ligand.

9. The method according to claim 1 wherein the steptavidin-metal particle complex comprises one or more particles of gold, silver, iron, nickel, gadolinium, lead, uranium, caesium, platinum, palladium, rhodium, technetium, tellurium, selenium, silicon (silicium), cupper, tin, rhenium, europium, aluminium, germanium, chromium, cadmium, niobium, titanium, magnesium, manganese, molybdenum, antimony, americium, lithium, and/or wolfram.

10. The method according to claim 1 wherein said steptavidin-metal particle complex comprises one or more streptavidin-gold particles.

11. The method according to claim 1 wherein the metal particles of said steptavidin-metal particle complex have a diameter between 0.6 to 40 nm.

12. The method according to claim 1 wherein said streptavidin-metal particle complex comprises streptavidin- and/or avidin-metal particle complex.

13. The method according to claim 1 wherein at least one probe is capable of binding to Human Papillomavirus.

14. The method according to claim 1 wherein said probe is capable of binding to Human Papillomavirus coat polypeptide.

15. The method according to claim 1 wherein at least one probe is capable of binding to a gene selected from the group consisting of HPV 16, HPV18, HPV 31, HPV 33, HPV 35, HPV 52 and HPV 58.

* * * * *